US006337430B1

(12) United States Patent
Ishige et al.

(10) Patent No.: US 6,337,430 B1
(45) Date of Patent: Jan. 8, 2002

(54) PLANT PROMOTERS

(75) Inventors: Fumiharu Ishige, Kobe; Eijiro Watanabe, Takarazuka; Kenji Oeda, Kyoto, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/561,825

(22) Filed: Apr. 28, 2000

(30) Foreign Application Priority Data

Apr. 30, 1999 (JP) .......................................... 11-124527
Sep. 1, 1999 (JP) .......................................... 11-247211

(51) Int. Cl.[7] ........................ C12N 15/82; C12N 15/00; C12P 19/34; C07H 21/04
(52) U.S. Cl. .................... 800/278; 435/468; 435/320.1; 435/91.1; 536/24.1
(58) Field of Search .............................. 435/320.1, 91.1, 435/419, 252.3, 468; 800/278, 295; 536/24.1

(56) References Cited

FOREIGN PATENT DOCUMENTS

| EP | 994186 A1 | 4/2000 |
|---|---|---|
| WO | WO 0024915 | 5/2000 |

*Primary Examiner*—James Ketter
*Assistant Examiner*—Lisa Gansheroff
(74) *Attorney, Agent, or Firm*—Birch, Stewart, Kolasch & Birch, LLP

(57) ABSTRACT

The present invention provides a promoter including the following DNA (a) or (b): (a) the DNA consisting of the nucleotide sequence of nucleotide numbers 1743 to 2301 in the nucleotide sequence represented by SEQ ID: No. 1; or, (b) the DNA which can be hybridized with said DNA (a) in a stringent condition and having a promoter function in a plant cell, and the like.

15 Claims, 4 Drawing Sheets

SEQUENCE LISTING

```
<160> NUMBER OF SEQ ID NOS: 30

<210> SEQ ID NO 1
<211> LENGTH: 2301
<212> TYPE: DNA
<213> ORGANISM: Glycine max cv. Williams 82
<220> FEATURE:
<221> NAME/KEY: promoter
<222> LOCATION: (1)..(2301)

<400> SEQUENCE: 1
atgcatctat aaaaattgta taataacaaa atgaattttg ttatgtattt tatttaataa       60
aattatgatt atgtgaaaag aataatttaa aaataaacaa aaattcattt tcttaatagg      120
aggccagaat aaattgcatg atgccaatta ggccaatagt aactcccaac cgttaaactt      180
gggcaaactg ttttccaatt cagtttggtt taagggagaa ttgtttttca attggcttta      240
attcgatttt ttgtgttgaa ctgaattgtg aacaagccta accaaggta atgaccctttt      300 tctcattcct agttcggttc aatttagaga ggaaaaattg aattcaattg tcccaaacta      360
atttgattcg aattttagaa tatagtgcat cgagccaaaa aaataattca attcggttga      420
actattttct aattcagttt ggttcgatct tctctactga atcaaaacca tgtacatact      480
tatttacaag tagtagcccc ccacatctaa acacaaagga tacatcaagc ttaattttaa      540
ccacacatga agaatcattt cctaaattaa tgcacactat tgtcagagaa atcacaaaaa      600
aaaaaaaaac accattgcag aggtgttaga tatataaaat tatcgtttta gatgagacta      660
tatacagaga gaaatatttt ttttaaaacc tgaagaatcc tctaataaag agcaatgtct      720
ctgagtattg aatttattta atggtccaaa ctcatttaac atatgttttt tttcatataa      780
atagatcatt tatgaaatca tatttatctt taaaaataat aatatttatc ttaaattttc      840
aatagaaaat gttctgataa atattaaatt aaaagcaaaa tacattttac tttttattta      900
agaatagagc tactttaaaa agattctttt ccttttacga ataaatcatt cgatatgact      960 acactttgt gttttgtttt ctttctttct ttttactatg aagtttttct ggaactagag      1020
atctctagag ttttctagtg ggacaaaaca gtgctgccgt gcgggttatc cattataaaa      1080
ctattgttcg atgaaccaaa aagactatta aaatatgttt tagtattcat tttaatatgc      1140
tttacattta aatttataaa caaactcttg tataatagtt ttttcatgaa ataaatgttt      1200
aattaacttt ttttttacat ttttttttacg gaataatact tatctcattt attataaatt      1260
aaatattcaa taaaaaaaat tataggatcg ataagataga gactaatgaa gaatgaaatc      1320
acccttacta acatatttat catttttctt catcacttta cttattgcat ctttttatttt     1380 ccccgtttct ctatatatat atatgcagga aatgagtgta acaaactaag aatcgtcctt      1440
```

```
gaagaaaaca tacttagcat atctaaacac gacaaacggt gccttctggc ttctacgtag    1500
atagataagg cttgattgcc gagggataaa gcaataagtc tcctctcgaa tgtgtccacc    1560
gaaaccatat tagtactaat taaatataag accccaggca aggccaaaaa gagctacccc    1620
ttgaaaacaa aacaaactcc atattatcaa gcatttaaga aataagattt gtttatatca    1680
tgtctaagtt tttaattaaa taattcaac acatgaaatt tactctaaat cttttatttt    1740
acatatgatg caaacaaatc ttatctgaat atttaattta actaatgcct attattttta    1800
gtcagattat acaatctagc tagtacttta ttttttctat cacgtacatc caatatcatt    1860
tttttcatag cagttcatga aatattttat taaatattaa ttaaagcata atttgacctc    1920
taaggtgtga cacgtgtaac taatatagct ttgattttt tttattatgg tttattttat    1980
attcaaaatc tatcctgatt taaattctaa ataatggatt aaaaaacata aattactaca    2040
ctaatcgagt caacaattat tactgtcgtc ggttcaactt tgagcttta agtatatgag    2100 agtggttgaa ttgctgccta tatgaataaa acaatattta tgggggataa aaatgagtct    2160
catattgtac atggtagttt gactttgaca catatacctt tgctctggc tgtaactaga    2220 atgcactagg cacaattaaa caaaaataaa ttctccttct ctatataaac ccaccatgtc    2280
accacaccct acccagcaaa a                                              2301
```

```
<210> SEQ ID NO 2
<211> LENGTH: 35
<212> TYPE: DNA
<213> ORGANISM: Artificial
<220> FEATURE:
<223> OTHER INFORMATION: Oligonucleotide (SRS-5) primer targeted to
      Glycine max cv. Williams designed for PCR

<400> SEQUENCE: 2
actaatgcat acccgtatca gttgcttaga gaagc                               35

<210> SEQ ID NO 3
<211> LENGTH: 25
<212> TYPE: DNA
<213> ORGANISM: Artificial
<220> FEATURE:
<223> OTHER INFORMATION: Oligonucleotide (SRS-5R) primer targeted to
      Glycine max cv. Williams designed for PCR

<400> SEQUENCE: 3
catgcaaacg tccacgtaat catcc                                          25

<210> SEQ ID NO 4
<211> LENGTH: 25
<212> TYPE: DNA
<213> ORGANISM: Artificial
<220> FEATURE:
<223> OTHER INFORMATION: Oligonucleotide (SRS-6) primer targeted to
      Glycine max cv. Williams designed for PCR

<400> SEQUENCE: 4
agctgcttat acgtccacgt tggcc                                          25

<210> SEQ ID NO 5
<211> LENGTH: 35
<212> TYPE: DNA
<213> ORGANISM: Artificial
<220> FEATURE:
<223> OTHER INFORMATION: Oligonucleotide (SRS-6R) primer targeted to
      Glycine max cv. Williams designed for PCR

<400> SEQUENCE: 5
```
actaatgcat gttgcaggga ggctcggaac gaggc                                    35

<210> SEQ ID NO 6
<211> LENGTH: 30
<212> TYPE: DNA
<213> ORGANISM: Artificial
<220> FEATURE:
<223> OTHER INFORMATION: Oligonucleotide primer targeted to Glycine max
      cv. Williams designed for PCR

<400> SEQUENCE: 6
atccttgaat tcagtcccat ggctccaagc                                          30

<210> SEQ ID NO 7
<211> LENGTH: 30
<212> TYPE: DNA
<213> ORGANISM: Artificial
<220> FEATURE:
<223> OTHER INFORMATION: Oligonucleotide primer targeted to Glycine max
      cv. Williams designed for PCR

<400> SEQUENCE: 7
cttggagcca tgggactgaa ttcaaggatc                                          30

<210> SEQ ID NO 8
<211> LENGTH: 22
<212> TYPE: DNA
<213> ORGANISM: Artificial
<220> FEATURE:
<223> OTHER INFORMATION: Oligonucleotide primer (SRS-15) targeted to
      Glycine max cv. Williams designed for PCR

<400> SEQUENCE: 8
ggaaatgatt cttcatgtgt gg                                                  22

<210> SEQ ID NO 9
<211> LENGTH: 24
<212> TYPE: DNA
<213> ORGANISM: Artificial
<220> FEATURE:
<223> OTHER INFORMATION: Oligonucleotide primer (SRS-16) targeted to
      Glycine max cv. Williams designed for PCR

<400> SEQUENCE: 9
taaccacaca tgaagaatca tttc                                                24

<210> SEQ ID NO 10
<211> LENGTH: 24
<212> TYPE: DNA
<213> ORGANISM: Artificial
<220> FEATURE:
<223> OTHER INFORMATION: Oligonucleotide primer (SRS-17) targeted to
      Glycine max cv. Williams designed for PCR

<400> SEQUENCE: 10
tttataatgg ataacccgca cggc                                                24

<210> SEQ ID NO 11
<211> LENGTH: 24
<212> TYPE: DNA
<213> ORGANISM: Artificial
<220> FEATURE:
<223> OTHER INFORMATION: Oligonucleotide primer (SRS-18) targeted to
      Glycine max cv. Williams designed for PCR

<400> SEQUENCE: 11
gactaatgaa gaatgaaatc accc                                      24

<210> SEQ ID NO 12
<211> LENGTH: 24
<212> TYPE: DNA
<213> ORGANISM: Artificial
<220> FEATURE:
<223> OTHER INFORMATION: Oligonucleotide primer (SRS-19) targeted to
      Glycine max cv. Williams designed for PCR

<400> SEQUENCE: 12
tcttaaatgc ttgataatat ggag                                      24

<210> SEQ ID NO 13
<211> LENGTH: 24
<212> TYPE: DNA
<213> ORGANISM: Artificial
<220> FEATURE:
<223> OTHER INFORMATION: Oligonucleotide primer (SRS-20) targeted to
      Glycine max cv. Williams designed for PCR

<400> SEQUENCE: 13
ttgacctcta aggtgtgaca cgtg                                      24

<210> SEQ ID NO 14
<211> LENGTH: 30
<212> TYPE: DNA
<213> ORGANISM: Artificial
<220> FEATURE:
<223> OTHER INFORMATION: Oligonucleotide primer targeted to Glycine max
      v. Williams designed for PCR

<400> SEQUENCE: 14
aaataaattc aatactcaga gacattgctc                                30

<210> SEQ ID NO 15
<211> LENGTH: 27
<212> TYPE: DNA
<213> ORGANISM: Artificial
<220> FEATURE:
<223> OTHER INFORMATION: Oligonucleotide primer targeted to Glycine max
      v. Williams designed for PCR

<400> SEQUENCE: 15
tttttctgga actagagatc tctagag                                   27

<210> SEQ ID NO 16
<211> LENGTH: 27
<212> TYPE: DNA
<213> ORGANISM: Artificial
<220> FEATURE:
<223> OTHER INFORMATION: Oligonucleotide primer (SRS-27) targeted to
      Glycine max cv. Williams designed for PCR

<400> SEQUENCE: 16
gtcaacaatt attactgtcg tcggttc                                   27

<210> SEQ ID NO 17
<211> LENGTH: 30
<212> TYPE: DNA
<213> ORGANISM: Artificial
<220> FEATURE:
<223> OTHER INFORMATION: Oligonucleotide primer (SRS-31) targeted to
      Glycine max cv. Williams designed for PCR

<400> SEQUENCE: 17
tgtgaacaag cctaaccaaa ggtaatgacc                                30

<210> SEQ ID NO 18
<211> LENGTH: 29
<212> TYPE: DNA
<213> ORGANISM: Artificial
<220> FEATURE:
<223> OTHER INFORMATION: Oligonucleotide primer targeted to Glycine max
      v. Williams designed for PCR

<400> SEQUENCE: 18
ttacatatga tgcaaacaaa tcttatctg                                29

<210> SEQ ID NO 19
<211> LENGTH: 30
<212> TYPE: DNA
<213> ORGANISM: Artificial
<220> FEATURE:
<223> OTHER INFORMATION: Oligonucleotide primer (SRS-N) targeted to
      Glycine max cv. Williams designed for PCR

<400> SEQUENCE: 19
catggctcca agcataagca aaactgtgga                               30

<210> SEQ ID NO 20
<211> LENGTH: 30
<212> TYPE: DNA
<213> ORGANISM: Artificial
<220> FEATURE:
<223> OTHER INFORMATION: Oligonucleotide primer (4RV) targeted to
      Glycine max cv. Williams designed for PCR

<400> SEQUENCE: 20
gacacccttg gagccaatac gtgccatttg                               30

<210> SEQ ID NO 21
<211> LENGTH: 30
<212> TYPE: DNA
<213> ORGANISM: Artificial
<220> FEATURE:
<223> OTHER INFORMATION: Oligonucleotide primer (seq1) targeted to
      Glycine max cv. Williams designed for PCR

<400> SEQUENCE: 21
cgggtggcaa gccatttgtc acgacgagga                               30

<210> SEQ ID NO 22
<211> LENGTH: 36
<212> TYPE: DNA
<213> ORGANISM: Artificial
<220> FEATURE:
<223> OTHER INFORMATION: Oligonucleotide primer (C2pst) targeted to
      Glycine max cv. Williams designed for PCR

<400> SEQUENCE: 22
taactgcaga aagagagtca aacatcatag tatccc                        36

<210> SEQ ID NO 23
<211> LENGTH: 2498
<212> TYPE: DNA
<213> ORGANISM: Glycine max cv. Williams 82
<220> FEATURE:
<221> NAME/KEY: CDS
<222> LOCATION: (62)..(2407)

<400> SEQUENCE: 23
ccaaaccata gcaaacctaa gcaccaaacc tctttctttc aagatccttg aattcagtcc    60

```
c atg gct cca agc ata agc aaa act gtg gaa cta aat tca ttt ggt ctt      109
  Met Ala Pro Ser Ile Ser Lys Thr Val Glu Leu Asn Ser Phe Gly Leu
   1               5                  10                  15 gtc aac ggt aat ttg cct ttg tcc ata acc cta gaa gga tca aat ttc        157
Val Asn Gly Asn Leu Pro Leu Ser Ile Thr Leu Glu Gly Ser Asn Phe
            20                  25                  30 ctc gcc aac ggc cac cct ttt ctc acg gaa gtt ccc gaa aac ata ata        205
Leu Ala Asn Gly His Pro Phe Leu Thr Glu Val Pro Glu Asn Ile Ile
        35                  40                  45 gtc acc cct tca ccc atc gac gcc aag agt agt aag aac aac gag gac        253
Val Thr Pro Ser Pro Ile Asp Ala Lys Ser Ser Lys Asn Asn Glu Asp
 50                  55                  60 gac gac gtc gta ggt tgc ttc gtg ggc ttc cac gcg gac gag ccc aga        301
Asp Asp Val Val Gly Cys Phe Val Gly Phe His Ala Asp Glu Pro Arg
 65                  70                  75                  80 agc cga cac gtg gct tcc ctg ggg aag ctc aga gga ata aaa ttc atg        349
Ser Arg His Val Ala Ser Leu Gly Lys Leu Arg Gly Ile Lys Phe Met
                85                  90                  95 agc ata ttc cgg ttt aag gtg tgg tgg acc act cac tgg gtc ggt agc        397
Ser Ile Phe Arg Phe Lys Val Trp Trp Thr Thr His Trp Val Gly Ser
            100                 105                 110 aac gga cac gaa ctg gag cac gag aca cag atg atg ctt ctc gac aaa        445
Asn Gly His Glu Leu Glu His Glu Thr Gln Met Met Leu Leu Asp Lys
        115                 120                 125 aac gac cag ctc gga cgc ccc ttt gtg ttg att ctc ccg atc ctc caa        493
Asn Asp Gln Leu Gly Arg Pro Phe Val Leu Ile Leu Pro Ile Leu Gln
130                 135                 140 gcc tcg ttc cga gcc tcc ctg caa ccc ggt ttg gat gat tac gtg gac        541
Ala Ser Phe Arg Ala Ser Leu Gln Pro Gly Leu Asp Asp Tyr Val Asp
145                 150                 155                 160 gtt tgc atg gag agc ggg tcg aca cgt gtc tgt ggc tcc agc ttc ggg        589
Val Cys Met Glu Ser Gly Ser Thr Arg Val Cys Gly Ser Ser Phe Gly
                165                 170                 175 agc tgc tta tac gtc cac gtt ggc cat gac ccg tat cag ttg ctt aga        637
Ser Cys Leu Tyr Val His Val Gly His Asp Pro Tyr Gln Leu Leu Arg
            180                 185                 190 gaa gca act aaa gtc gtt agg atg cat ttg ggg acg ttc aag ctt ctc        685
Glu Ala Thr Lys Val Val Arg Met His Leu Gly Thr Phe Lys Leu Leu
        195                 200                 205 gag gag aaa acc gcg cca gtg atc ata gac aag ttt ggt tgg tgt aca        733
Glu Glu Lys Thr Ala Pro Val Ile Ile Asp Lys Phe Gly Trp Cys Thr
    210                 215                 220 tgg gac gcg ttt tac ttg aag gtg cat ccc tca ggt gtg tgg gaa ggg        781
Trp Asp Ala Phe Tyr Leu Lys Val His Pro Ser Gly Val Trp Glu Gly
225                 230                 235                 240 gtg aaa ggg ttg gtg gag gga ggg tgc cct cca ggg atg gtc cta atc        829
Val Lys Gly Leu Val Glu Gly Gly Cys Pro Pro Gly Met Val Leu Ile
                245                 250                 255 gac gac ggg tgg caa gcc att tgt cac gac gag gac ccc ata acg gac        877
Asp Asp Gly Trp Gln Ala Ile Cys His Asp Glu Asp Pro Ile Thr Asp
            260                 265                 270 caa gag ggt atg aag cga acc tcc gca ggg gag caa atg cca tgc agg        925
Gln Glu Gly Met Lys Arg Thr Ser Ala Gly Glu Gln Met Pro Cys Arg
        275                 280                 285 ttg gtg aag ttg gag gaa aat tac aag ttc aga cag tat tgt agt gga        973
Leu Val Lys Leu Glu Glu Asn Tyr Lys Phe Arg Gln Tyr Cys Ser Gly
    290                 295                 300 aag gat tct gag aag ggt atg ggt gcc ttt gtt agg gac ttg aag gaa       1021
Lys Asp Ser Glu Lys Gly Met Gly Ala Phe Val Arg Asp Leu Lys Glu
305                 310                 315                 320
```

-continued

```
cag ttt agg agc gtg gag cag gtg tat gtg tgg cac gcg ctt tgt ggg    1069
Gln Phe Arg Ser Val Glu Gln Val Tyr Val Trp His Ala Leu Cys Gly
            325                 330                 335 tat tgg ggt ggg gtc aga ccc aag gtt ccg ggc atg ccc cag gct aag    1117
Tyr Trp Gly Gly Val Arg Pro Lys Val Pro Gly Met Pro Gln Ala Lys
        340                 345                 350 gtt gtc act ccg aag ctg tcc aat gga cta aaa ttg aca atg aag gat    1165
Val Val Thr Pro Lys Leu Ser Asn Gly Leu Lys Leu Thr Met Lys Asp
    355                 360                 365 tta gcg gtg gat aag atc gtc agt aac gga gtt gga ctg gtg cca cca    1213
Leu Ala Val Asp Lys Ile Val Ser Asn Gly Val Gly Leu Val Pro Pro
370                 375                 380 cac ctg gct cac ctt ttg tac gag ggc ctc cac tcc cgt ttg gaa tct    1261
His Leu Ala His Leu Leu Tyr Glu Gly Leu His Ser Arg Leu Glu Ser
385                 390                 395                 400 gcg ggt att gac ggt gtt aag gtt gac gtt ata cac ttg ctc gag atg    1309
Ala Gly Ile Asp Gly Val Lys Val Asp Val Ile His Leu Leu Glu Met
                405                 410                 415 cta tcc gag gaa tac ggt ggc cgt gtt gag cta gcc aaa gct tat tac    1357
Leu Ser Glu Glu Tyr Gly Gly Arg Val Glu Leu Ala Lys Ala Tyr Tyr
            420                 425                 430 aaa gcg ctc act gct tcg gtg aag aag cat ttc aaa ggc aat ggg gtc    1405
Lys Ala Leu Thr Ala Ser Val Lys Lys His Phe Lys Gly Asn Gly Val
        435                 440                 445 att gcg agc atg gag cat tgt aat gac ttc ttt ctc ctt ggt acc gaa    1453
Ile Ala Ser Met Glu His Cys Asn Asp Phe Phe Leu Leu Gly Thr Glu
    450                 455                 460 gcc ata gcc ctt ggg cgc gta gga gat gat ttt tgg tgc act gat ccc    1501
Ala Ile Ala Leu Gly Arg Val Gly Asp Asp Phe Trp Cys Thr Asp Pro
465                 470                 475                 480 tct gga gat cca aat ggc acg tat tgg ctc caa ggg tgt cac atg gtg    1549
Ser Gly Asp Pro Asn Gly Thr Tyr Trp Leu Gln Gly Cys His Met Val
                485                 490                 495 cac tgt gcc tac aac agc ttg tgg atg ggg aat ttt att cag ccg gat    1597
His Cys Ala Tyr Asn Ser Leu Trp Met Gly Asn Phe Ile Gln Pro Asp
            500                 505                 510 tgg gac atg ttc cag tcc act cac cct tgt gcc gaa ttc cat gca gcc    1645
Trp Asp Met Phe Gln Ser Thr His Pro Cys Ala Glu Phe His Ala Ala
        515                 520                 525 tct agg gcc atc tct ggt gga cca gtt tac gtt agt gat tgt gtt gga    1693
Ser Arg Ala Ile Ser Gly Gly Pro Val Tyr Val Ser Asp Cys Val Gly
    530                 535                 540 aag cac aac ttc aag ttg ctc aag agc ctc gct ttg cct gat ggg acg    1741
Lys His Asn Phe Lys Leu Leu Lys Ser Leu Ala Leu Pro Asp Gly Thr
545                 550                 555                 560 att ttg cgt tgt caa cac tat gca ctc ccc aca cga gac tgt ttg ttt    1789
Ile Leu Arg Cys Gln His Tyr Ala Leu Pro Thr Arg Asp Cys Leu Phe
                565                 570                 575 gaa gac ccc ttg cat gat ggg aag aca atg ctc aaa att tgg aat ctc    1837
Glu Asp Pro Leu His Asp Gly Lys Thr Met Leu Lys Ile Trp Asn Leu
            580                 585                 590 aac aaa tat aca ggt gtt ttg ggt cta ttt aat tgc caa gga ggt ggg    1885
Asn Lys Tyr Thr Gly Val Leu Gly Leu Phe Asn Cys Gln Gly Gly Gly
        595                 600                 605 tgg tgt ccc gta act agg aga aac aag agt gcc tct gaa ttt tca caa    1933
Trp Cys Pro Val Thr Arg Arg Asn Lys Ser Ala Ser Glu Phe Ser Gln
    610                 615                 620 act gtg aca tgc tta gcg agt cct caa gac att gaa tgg agc aat ggg    1981
Thr Val Thr Cys Leu Ala Ser Pro Gln Asp Ile Glu Trp Ser Asn Gly
```

```
                625                 630                 635                 640
aaa agc cca ata tgc ata aaa ggg atg aat gtg ttt gct gta tat ttg        2029
Lys Ser Pro Ile Cys Ile Lys Gly Met Asn Val Phe Ala Val Tyr Leu
                        645                 650                 655 ttc aag gac cac aaa cta aag ctc atg aag gca tca gag aaa ttg gaa        2077
Phe Lys Asp His Lys Leu Lys Leu Met Lys Ala Ser Glu Lys Leu Glu
                660                 665                 670 gtt tca ctt gag cca ttt act ttt gag cta ttg aca gtg tct cca gtg        2125
Val Ser Leu Glu Pro Phe Thr Phe Glu Leu Leu Thr Val Ser Pro Val
            675                 680                 685 att gtg ctg tca aaa aag tta att caa ttt gct cca att gga tta gtg        2173
Ile Val Leu Ser Lys Lys Leu Ile Gln Phe Ala Pro Ile Gly Leu Val
        690                 695                 700 aac atg ctt aac act ggt ggt gcc att cag tcc atg gag ttt gac aac        2221
Asn Met Leu Asn Thr Gly Gly Ala Ile Gln Ser Met Glu Phe Asp Asn
705                 710                 715                 720 cac ata gat gtg gtc aaa att ggg gtt agg ggt tgt ggg gag atg aag        2269
His Ile Asp Val Val Lys Ile Gly Val Arg Gly Cys Gly Glu Met Lys
                725                 730                 735 gtg ttt gca tca gag aaa cca gtt agt tgc aaa cta gat ggg gta gtt        2317
Val Phe Ala Ser Glu Lys Pro Val Ser Cys Lys Leu Asp Gly Val Val
                740                 745                 750 gta aaa ttt gat tat gag gat aaa atg ctg aga gtg caa gtt ccc tgg        2365
Val Lys Phe Asp Tyr Glu Asp Lys Met Leu Arg Val Gln Val Pro Trp
            755                 760                 765 cct agt gct tca aaa ttg tca atg gtt gag ttt tta ttt tga              2407
Pro Ser Ala Ser Lys Leu Ser Met Val Glu Phe Leu Phe
        770                 775                 780 tccctgaagg tgaatttggg atactatgat gtttgactct cttttaagt aataagagtc     2467 atattttct gttgtaaaaa aaaaaaaaa a                                      2498
```

<210> SEQ ID NO 24
<211> LENGTH: 27
<212> TYPE: DNA
<213> ORGANISM: Artificial
<220> FEATURE:
<223> OTHER INFORMATION: Oligonucleotide primer (lucl) targeted to
    Glycine max cv. Williams designed for PCR

<400> SEQUENCE: 24
aatgttcata ctgttgagca attcacg                                         27

<210> SEQ ID NO 25
<211> LENGTH: 25
<212> TYPE: DNA
<213> ORGANISM: Artificial
<220> FEATURE:
<223> OTHER INFORMATION: Oligonucleotide primer (SRS-21) targeted to
    Glycine max cv. Williams designed for PCR

<400> SEQUENCE: 25
aaacgtccac gtaatcatcc aaacc                                           25

<210> SEQ ID NO 26
<211> LENGTH: 2361
<212> TYPE: DNA
<213> ORGANISM: Glycine max cv. Williams 82
<220> FEATURE:
<221> NAME/KEY: promoter
<222> LOCATION: (1)..(2361)

<400> SEQUENCE: 26

-continued

| | |
|---|---|
| atgcatctat aaaaattgta taataacaaa atgaattttg ttatgtattt tatttaataa | 60 |
| aattatgatt atgtgaaaag ataatttaa aaataaacaa aaattcattt tcttaatagg | 120 |
| aggccagaat aaattgcatg atgccaatta ggccaatagt aactcccaac cgttaaactt | 180 |
| gggcaaactg tttccaatt cagtttggtt taagggagaa ttgttttca attggcttta | 240 |
| attcgatttt ttgtgttgaa ctgaattgtg aacaagccta accaaggta atgaccctt | 300 |
| tctcattcct agttcggttc aatttagaga ggaaaaattg aattcaattg tcccaaacta | 360 |
| atttgattcg aattttagaa tatagtgcat cgagccaaaa aataattca attcggttga | 420 |
| actatttct aattcagttt ggttcgatct tctctactga atcaaaacca tgtacatact | 480 |
| tatttacaag tagtagcccc ccacatctaa acacaaagga tacatcaagc ttaattttaa | 540 |
| ccacacatga agaatcattt cctaaattaa tgcacactat tgtcagagaa atcacaaaaa | 600 |
| aaaaaaaaac accattgcag aggtgttaga tatataaaat tatcgtttta gatgagacta | 660 |
| tatacagaga gaaaatattt ttttaaaacc tgaagaatcc tctaataaag agcaatgtct | 720 |
| ctgagtattg aatttattta atggtccaaa ctcatttaac atatgttttt tttcatataa | 780 |
| atagatcatt tatgaaatca tatttatctt taaaaataat aatatttatc ttaaattttc | 840 |
| aatagaaaat gttctgataa atattaaatt aaaagcaaaa tacattttac ttttattta | 900 |
| agaatagagc tactttaaaa agattctttt ccttttacga ataaatcatt cgatatgact | 960 |
| acactttgt gttttgtttt ctttctttct ttttactatg aagttttct ggaactagag | 1020 |
| atctctagag ttttctagtg ggacaaaaca gtgctgccgt gcgggttatc cattataaaa | 1080 |
| ctattgttcg atgaaccaaa aagactatta aatatgtttt tagtattcat tttaatatgc | 1140 |
| tttacattta aatttataaa caaactcttg tataatagtt ttttcatgaa ataaatgttt | 1200 |
| aattaacttt ttttacatt tttttacgg aataatactt atctcattta ttataaatta | 1260 |
| aatattcaat aaaaaaatt ataggatcga tagaatagag actaatgaag aatgaaatca | 1320 |
| cccttactaa catatttatt atttttcttc atcactttac ttattgcatc ttttattttc | 1380 |
| cccgtttctc tatatatata tatgcaggaa atgagtgtaa caaactaaga atcgtccttg | 1440 |
| aagaaaacat acttagcata tctaaacacg acaaacggtg ccttctggct tctacgtaga | 1500 |
| tagataaggc ttgattgccg agggataaag caataagtct cctctcgaat gtgtccaccg | 1560 |
| aaaccatatt agtactaatt aaatataaga ccccaagcaa ggccaaaaag agctacccct | 1620 |
| tgaaaacaaa acaaactcca tattatcaag catttaagaa ataagatttg tttatatcat | 1680 |
| gtctaagttt ttaattaaat aaattcaaca catgaaattt actctaaatc tttatattta | 1740 |
| catatgatgc aaacaaatct tatctgaata tttaatttaa ctaatgccta ttatttttag | 1800 |
| tcagattata caatctagct agtactttat tttttctatc acgtacatcc aatatcattt | 1860 |
| ttttcatagc agttcatgaa atattttatt aaatattaat taaagcataa tttgacctct | 1920 |
| aaggtgtgac acgtgtaact aatatagctt tgattttttt ttattatggt ttattttata | 1980 |
| ttcaaaatct atcctgattt aaattctaaa taatggatta aaaaacataa attactacac | 2040 |
| taattgagtc aacaattatt actgtcgtcg gttcaacttt gagcttttaa gtatatgaga | 2100 |
| gtggttgaat tgctgcctat atgaataaaa caatatttat gggggataaa aatgagtctc | 2160 |
| atattgtaca tggtagtttg actttgacac atatacccctt tgctctggct gtaactagaa | 2220 |
| tgcactaggc acaattaaac aaaaataaat tctccttctc tatataaacc caccatgtca | 2280 |
| ccacacccta cccagcaaaa ccaaaccata gcaaacctaa gcaccaaacc tctttctttc | 2340 |
| aagatccttg aattcagtcc c | 2361 |

<210> SEQ ID NO 27
<211> LENGTH: 2362
<212> TYPE: DNA
<213> ORGANISM: Glycine max cv. Williams 82
<220> FEATURE:
<221> NAME/KEY: promoter
<222> LOCATION: (1)..(2362)

<400> SEQUENCE: 27

| | | | | | |
|---|---|---|---|---|---|
| atgcatctat | aaaaattgta | taataacaaa | atgaattttg | ttatgtattt | tatttaataa | 60 |
| aattatgatt | atgtgaaaag | aataatttaa | aaataaacaa | aaattcattt | tcttaatagg | 120 |
| aggccagaat | aaattgcatg | atgccaatta | ggccaatagt | aactcccaac | cgttaaactt | 180 |
| gggcaaactg | ttttccaatt | cagtttggtt | taagggagaa | ttgttttca | attggcttta | 240 |
| attcgatttt | ttgtgttgaa | ctgaattgtg | aacaagccta | accaaggta | atgaccctt | 300 |
| tctcattcct | agttcggttc | aatttagaga | ggaaaaattg | aattcaattg | tcccaaacta | 360 |
| atttgattcg | aattttagaa | tatagtgcat | cgagccaaaa | aataattca | attcggttga | 420 |
| actatttct | aattcagttt | ggttcgatct | tctctactga | atcaaaacca | tgtacatact | 480 |
| tatttacaag | tagtagcccc | ccacatctaa | acacaaagga | tacatcaagc | ttaattttaa | 540 |
| ccacacatga | agaatcattt | cctaaattaa | tgcacactat | tgtcagagaa | atcacaaaaa | 600 |
| aaaaaaaaac | accattgcag | aggtgttaga | tatataaaat | tatcgttta | gatgagacta | 660 |
| tatacagaga | gaaatatt | ttttaaaacc | tgaagatcc | tctaataaag | agcaatgtct | 720 |
| ctgagtattg | aatttattta | atggtccaaa | ctcatttaac | atatgttttt | tttcatataa | 780 |
| atagatcatt | tatgaaatca | tatttatctt | taaaaataat | aatatttatc | ttaaattttc | 840 |
| aatagaaaat | gttctgataa | atattaaatt | aaaagcaaaa | tacattttac | tttttattta | 900 |
| agaatagagc | tactttaaaa | agattctttt | ccttttacga | ataaatcatt | cgatatgact | 960 |
| acacttttgt | gttttgtttt | ctttctttct | ttttactatg | aagttttct | ggaactagag | 1020 |
| atctctagag | ttttctagtg | ggacaaaaca | gtgctgccgt | gcgggttatc | cattataaaa | 1080 |
| ctattgttcg | atgaaccaaa | aagactatta | aaatatgttt | tagtattcat | tttaatatgc | 1140 |
| tttacattta | aattataaa | caactcttg | tataatagtt | ttttcatgaa | ataaatgttt | 1200 |
| aattaactt | ttttttacat | ttttttacg | gaataatact | tatctcattt | attataaatt | 1260 |
| aaatattcaa | taaaaaaat | taaggatcg | atagaataga | gactaatgaa | gaatgaaatc | 1320 |
| acccttacta | acatatttat | catttttctt | catcacttta | cttattgcat | cttttatttt | 1380 |
| ccccgtttct | ctatatatat | atatgcagga | aatgagtgta | acaaactaag | aatcgtcctt | 1440 |
| gaagaaaaca | tacttagcat | atctaaacac | gacaaacggt | gccttctggc | ttctacgtag | 1500 |
| atagataagg | cttgattgcc | gagggataaa | gcaataagtc | tcctctcgaa | tgtgtccacc | 1560 |
| gaaaccatat | tagtactaat | taaatataag | accccaggca | aggccaaaaa | gagctacccc | 1620 |
| ttgaaaacaa | aacaaactcc | atattatcaa | gcatttaaga | ataagatttt | gtttatatca | 1680 |
| tgtctaagtt | tttaattaaa | taaattcaac | acatgaaatt | tactctaaat | ctttatattt | 1740 |
| acatatgatg | caaacaaatc | ttatctgaat | atttaattta | actaatgcct | attatttta | 1800 |
| gtcagattat | acaatctagc | tagtacttta | ttttttctat | cacgtacatc | caatatcatt | 1860 |
| tttttcatag | cagttcatga | aatatttat | taaatattaa | ttaaagcata | atttgacctc | 1920 |
| taaggtgtga | cacgtgtaac | taatatagct | ttgattttt | tttattatgg | tttattttat | 1980 |
| attcaaaatc | tatcctgatt | taaattctaa | ataatggatt | aaaaaacata | aattactaca | 2040 |

-continued

```
ctaatcgagt caacaattat tactgtcgtc ggttcaactt tgagctttta agtatatgag    2100
agtggttgaa ttgctgccta tatgaataaa acaatattta tggggataaa aaatgagtct    2160
catattgtac atggtagttt gactttgaca catataccct ttgctctggc tgtaactaga    2220
atgcactagg cacaattaaa caaaaataaa ttctccttct ctatataaac ccaccatgtc    2280
accacaccct acccagcaaa accaaaccat agcaaaccta agcaccaaac cttttctttt    2340
caagatcctt gaattcaatc cc                                             2362
```

<210> SEQ ID NO 28
<211> LENGTH: 2363
<212> TYPE: DNA
<213> ORGANISM: Glycine max cv. Williams 82
<220> FEATURE:
<221> NAME/KEY: promoter
<222> LOCATION: (1)..(2363)

<400> SEQUENCE: 28

```
atgcatctat aaaaattgta taataacaaa atgaattttg ttatgtattt tatttaataa      60
aattatgatt atgtgaaaag aataatttaa aaataaacaa aaattcattt tcttaatagg     120
aggccagaat aaattgcatg atgccaatta ggccaatagt aactcccaac cgttaaactt     180
gggcaaactg ttttccaatt cagtttggtt taagggagaa ttgttttttca attggcttta    240 attcgatttt ttgtgttgaa ctgaattgtg aacaagccta accaaaggta atgacccttt     300
tctcattcct agttcggttc aatttagaga ggaaaaattg aattcaattg tcccaaacta    360
atttgattcg aattttagaa tatagtgcat cgagccaaaa aaataattca attcggttga    420
actattttct aattcagttt ggttcgatct tctctactga atcaaaacca tgtacatact    480
tatttacaag tagtagcccc ccacatctaa acacaaagga tacatcaagc ttaattttaa    540
ccacacatga agaatcattt ccttaaatta atgcacacta ttgtcagaga atcacaaaa    600 aaaaaaaaaa acaccattgc agaggtgtta gatatataaa attatcgttt tagatgagac    660
tatatacaga gagaaaatat ttttttaaaa cctgaagaat cctctaataa agagcaatgt    720
ctctgagtat tgaatttatt taatggtcca aactcattta acatatgttt tttttcatat    780
aaatagatca tttatgaaat catatttatc tttaaaaata ataatattta tcttaaattt    840
tcaatagaaa atgttctgat aaatattaaa ttaaaagcaa aatacatttt acttttttatt    900 taagaataga gctactttaa aaagattctt ttccttttac gaataaatca ttcgatatga    960
ctcacttttt gtgttttgtt ttcttctctt cttttttacta tgaagttttt ctggaactag    1020
agatctctag agttttctag tgggacaaaa cagagctgcc gtgcgggtta tccattataa    1080
aactattgtt cgatgaacca aaaagactat taaaatatgt tttagtattc attttaatat    1140
gctttacatt taaatttata aacaaactct tgtataatag tttttttcatg aaataaatgt    1200 ttaattaact ttttttttaca ttttttttac ggaataatac ttatctcatt tattataaat    1260
taaatattca ataaaaaaaa ttataggatc gatagaatag agactaatga agaatgaaat    1320 caccccttact aacatatttta ttattttttct tcatcacttt acttattgca tcttttattt    1380
tcccccgttc tctatatata tatatgcagg aaatgagtgt aacaaactaa gaatcgtcct    1440
tgaagaaaac atacttagca tatctaaaca cgacaaacgg tgccttctgg cttctacgta    1500
gatagataag gcttgattgc cgagggataa agcaataagt ctcctctcga atgtgtccac    1560
cgaaaccata ttagtactaa ttaaatataa gaccccaagc aaggccaaaa agagctaccc    1620
cttgaaaaca aaacaaactc catattatca agcatttaag aaataagatt tgtttatatc    1680
```

```
atgtctaagt ttttaattaa ataaattcaa cacatgaaat ttactctaaa tctttatatt    1740
tacatatgat gcaaacaaat cttatctgaa tatttaattt aactaatgcc tattattttt    1800
agtcagatta tacaatctag ctagtacttt attttttcta tcacgtacat ccaatatcat    1860 tttttcata gcagttcatg aaatatttta ttaaatatta attaaagcat aatttgacct     1920
ctaaggtgtg acacgtgtaa ctaatatagc tttgattttt tttattatg gtttatttta    1980 tattcaaaat ctatcctgat ttaaattcta aataatggat taaaaacat aaattactac    2040 actaattgag tcaacaatta ttactgtcgt cggttcaact ttgagctttt aagtatatga    2100
gagtggttga attgctgcct atatgaataa aacatatttt atgggggata aaaatgagtc    2160
tcatattgta catggtagtt tgactttgac acatataccc tttgctctgg ctgtaactag    2220
aatgcactag gcacaattaa acaaaaataa attctccttc tctatataaa cccaccatgt    2280
caccacaccc tacccagcaa aaccaaacca tagcaaacct aagcaccaaa cctctttctt    2340
tcaagatcct tgaattcagt ccc                                            2363

<210> SEQ ID NO 29
<211> LENGTH: 2361
<212> TYPE: DNA
<213> ORGANISM: Glycine max cv. Williams 82
<220> FEATURE:
<221> NAME/KEY: promoter
<222> LOCATION: (1)..(2361)

<400> SEQUENCE: 29
atgcatctat aaaaattgta taataacaaa atgaattttg ttatgtattt tatttaataa      60
aattatgatt atgtgaaaag aataatttaa aaataaacaa aaattcattt tcttaatagg    120
aggccagaat aaattgcatg atgccaatta ggccaatagt aactcccaac cgttaaactt    180
gggcaaactg ttttccaatt cagtttggtt taagggagaa ttgttttca attggcttta    240 attcgatttt ttgtgttgaa ctgaattgtg aacaagccta accaaaggta atgacccttt    300
tctcattcct agttcggttc aatttagaga ggaaaaattg aattcaattg tcccaaacta    360
atttgattcg aatttagaa tatagtgcgt cgagccaaaa aataattca attcggttga    420 actatttct aattcagttt ggttcgatct tctctactga atcaaaacca tgtacatact    480
tatttacaag tagtagccc ccacatctaa acacgaagga tacatcaagc ttaattttaa    540
ccacacatga agaatcattt cctaaattaa tgcacactat tgtcagagaa atcacaaaaa    600 aaaaaaaca ccattgcaga ggtgttagat atataaaatt atcgttttag atgagactat    660
atacagagag aaaatatctt tttaaaacct gaagaatcct ctaataaaga gcaatgtctc    720
tgagtattga atttatttaa tggtccaaac tcatttaaca tatgttttt tttatataaa    780 tagatcattt atgaaatcat atttatcttt aaaataata atatttatct taaattttca    840
atagaaaatg ttctgataaa tattaaatta aaagcaaaat acatttact ttttatttaa    900 gaatagagct actttaaaaa gattcttttc ctttttacgaa taaatcattc gatatgacta    960
cacttttgtg tttttgttttc tttctttctt tttactatga agtttttctg gaactagaga  1020
tctctagagt tttctagtgg gacaaaacag tgctgccgtg cgggttatcc attataaaaac  1080 tattgttcga tgaaccaaaa agactattaa atatgttttt agtattcatt ttaatatgct  1140
ttacatttaa atttataaac aaactcttgt ataaagtttt tttcatgaaa taaatgttta  1200 attaacttttt ttttttacatt tttttttacgg aataatactt atctcatttta ttataaaatta  1260 aatattcaat aaaaaaaaatt ataggatcga tagaatagag actaatgaag aatgaaatca  1320
```

```
cccttactaa catatttatt attttttcttc atcactttac ttattgcatc ttttattttc    1380
cccgtttctc tatatatata tatgcaggaa atgagtgtaa caaactaaga atcgtccttg    1440
aagaaaacat acttagcata tctaaacacg acaaacggtg ccttctggct tctacgtaga    1500
tagataaggc ctgattgccg agggataaag caataagtct cctctcgaat gtgtccaccg    1560
aaaccatatt agtactaatt aaatataaga ccccaagcaa ggccaaaaag agctacccct    1620
tgaaaacaaa acaaactcca tattatcaag catttaagaa ataagatttg tttatatcat    1680
gtctaagttt ttaattaaat aaattcaaca catgaaattt actctaaatc tttatattta    1740
catatgatgc aaacaaatct tatctgaata tttaatttaa ctaatgccta ttatttttag    1800
tcagattata caatctagct agtactttat tttttctatc acgtacatcc aatatcattt    1860
ttttcatagc agttcatgaa atattttatt aaatattaat taaagcataa tttgacctct    1920
aaggtgtgac acgtgtaact aatatagctt tgatttttt ttattatggt ttattttata    1980
ttcaaaatct atcctgattt aaattctaaa taatggatta aaaaacataa attactacac    2040
taattgagtc aacaattatt actgtcgtcg gttcaacttt gagcttttaa gtatatgaga    2100
gtggttgaat tgctgcctat atgaataaaa caatatttat gggggataaa aatgagtctc    2160
atattgtaca tggtagtttg actttgacac atatacccctt tgctctggct gtaactagaa    2220
tgcactaggc acaattaaac aaaaataaat tctccttctc tatataaacc caccatgtca    2280 ccacaccta cccagcaaaa ccaaaccata gcaaacctaa gcaccaaacc tccttctttc    2340
aagatccttg aattcagtcc c                                             2361

<210> SEQ ID NO 30
<211> LENGTH: 27
<212> TYPE: DNA
<213> ORGANISM: Artificial
<220> FEATURE:
<223> OTHER INFORMATION: Oligonucleotide primer (SRS-26) targeted to
      Glycine max cv. Williams designed for PCR

<400> SEQUENCE: 30
tttttctgga actagagatc tctagag                                          27
```

PLANT PROMOTERS

BACKGROUND OF THE INVENTION

1. Field of the Invention

The present invention relates to a plant promoter and the like.

2. Description of the Prior Art

A transformed plant with a useful property is attempted to be produced by introducing genes into a plant and allowing it to be expressed, and some of the transformed plants are employed practically.

In order to express a gene introduced into a plant, such gene is generally under the control of a promoter which is functional in the plant cell. In plant breeding as described above, the selection of a promoter having the characteristics suitable for the purpose of the breeding and the expression of the gene under the control of such promoter are required for a production of a transformed plant expressing a desired property.

SUMMARY OF THE INVENTION

Nevertheless, there are not sufficiently various types of the plant promoters which can be used in a plant breeding technology involving the gene introduction described above, and novel plant promoters are strongly expected to be developed.

Under the circumstance described above, the present inventors made an effort and finally found a novel DNA having a promoter function in a plant cell, and thus reaching the present invention.

Namely, the present invention provides:

1. a promoter comprising the following DNA (a) or (b):
   (a) the DNA consisting of the nucleotide sequence of nucleotide numbers 1743 to 2301 in the nucleotide sequence represented by SEQ ID: No.1; or,
   (b) the DNA which can be hybridized with said DNA (a) in a stringent condition and having a promoter function in a plant cell,
2. the promoter according to the above 1 comprising the following DNA (c), (d), (e) or (f):
   (c) the DNA consisting of the nucleotide sequence of nucleotide numbers 1020 to 2301 in the nucleotide sequence represented by SEQ ID: No.1;
   (d) the DNA consisting of the nucleotide sequence of nucleotide numbers 2 to 2301 in the nucleotide sequence represented by SEQ ID: No.1;
   (e) the DNA consisting of the nucleotide sequence represented by SEQ ID: No.1; or,
   (f) the DNA which can be hybridized with said DNA (c), (d) or (e) in a stringent condition and having a promoter function in a plant cell,
3. a chimeric gene constructed by ligating the promoter of the above 1, a desirable gene and a terminator in a functional form,
4. a vector comprising the promoter of the above 1,
5. the vector according to the above 4 comprising a gene insertion site and a terminator downstream of the promoter,
6. a vector comprising the chimeric gene of the above 3,
7. a transformant produced by introducing the promoter of the above 1 into a host cell,
8. a transformant produced by introducing the chimeric gene of the above 3 into a host cell,
9. a transformant produced by introducing the vector of the above 4 into a host cell,
10. the transformant according to the above 7 wherein the host cell is a microorganism cell,
11. the transformant according to the above 7 wherein the host cell is a plant cell,
12. a method for producing a chimeric gene comprising a step of ligating the promoter of the above 1, a desired gene and a terminator in a functional form,
13. a method for producing a vector which comprises a step of ligating the promoter of the above 1 and a desired gene in a functional form, and
14. a method for producing a transformed plant comprising a step of introducing the promoter of the above 1 into a plant cell and a step of expressing a gene under the control of the promoter of the above 1.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

Figure 1:
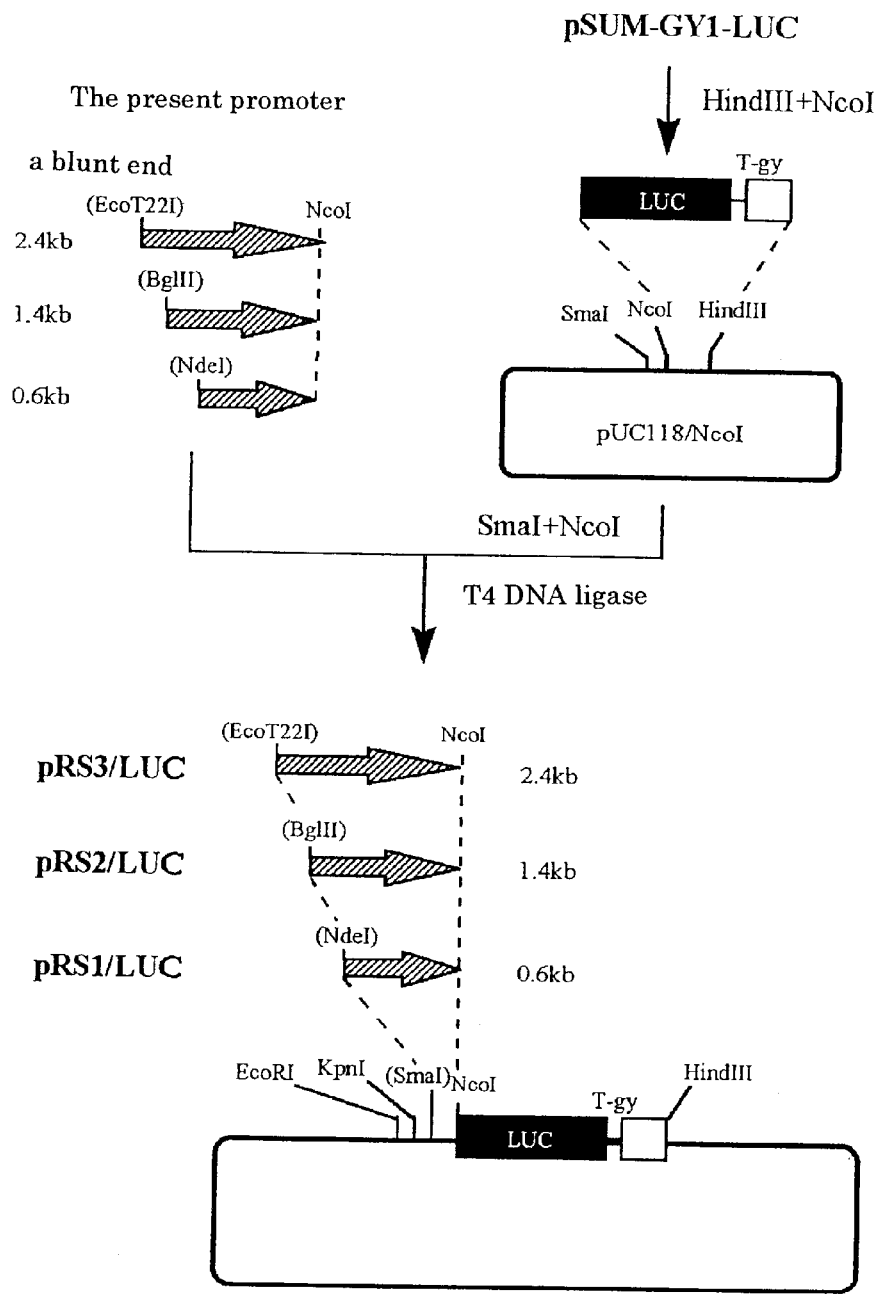
FIG. 1 shows the process for constructing the present vectors pRS1/LUC, pRS2/LUC and pRS3/LUC each comprising the present promoter. In this figure, LUC represents a firefly-derived luciferase gene, T-gy represents a soybean-derived glycinin gene terminator. A restriction enzyme site within a bracket indicates a modification of the restriction enzyme recognition sequence in which this restriction enzyme cannot conduct the digestion.

The present invention is further described in detail below. The gene engineering technology employed here can be practiced in accordance with a conventional method, such as one described in J., Sambrook, E., F., Frisch, T., Maniatis, Molecular cloning 2nd edition., Cold Spring Harbor Laboratory press (1989), and D., M., Glover, DNA Cloning, published by IRL (1985).

In the present invention, the term "promoter function" means an ability of acting as a promoter, i.e., an ability of initiating a gene transcription, and the term "plant promoter" means a DNA having a promoter function in a plant cell.

The present promoter comprises the following DNA (a) or (b): (a) the DNA consisting of the nucleotide sequence of nucleotide numbers 1743 to 2301 in the nucleotide sequence represented by SEQ ID: No.1; or, (b) the DNA which can be hybridized with said DNA (a) in a stringent condition and having a promoter function in a plant cell.

The DNA which is "hybridized in a stringent condition" is a DNA described below. Thus, such DNA is characterized in that (1) it forms a DNA-DNA hybrid with a DNA consisting of the nucleotide sequence of nucleotide numbers 1743 to 2301 in the nucleotide sequence represented by SEQ ID: NO. 1 by hybridization at 65° C. at a high ion concentration, for example, 6×SSC (900 mM sodium chloride, 90 mM sodium citrate) and the like and that (2) the resultant hybrid can be maintained even after washing for 30 minutes at 65° C. at a low ion concentration, for example, 0.1×SSC (15 mM sodium chloride, 1.5 mM sodium citrate) and the like. Typically, a DNA consisting of a nucleotide sequence in which a part of the nucleotide sequence represented by SEQ ID: No.1 is deleted, substituted or added, for example, the nucleotide sequence represented by SEQ ID: No.26, may be exemplified. Such DNA may be a DNA cloned from nature, a DNA obtained by an artificial deletion, substitution or addition of nucleotide(s) in a DNA cloned from nature, or a DNA which is synthesized artificially.

The present promoter may contain another DNA upstream and/or downstream of the present promoter DNA as long as the modified promoter is functional. Typically, for example, the followings:

the DNA consisting of the nucleotide sequence of nucleotide numbers 1020 to 2301 in the nucleotide sequence represented by SEQ ID: No.1;

the DNA consisting of the nucleotide sequence of nucleotide numbers 2 to 2301 in the nucleotide sequence represented by SEQ ID: No.1;

the DNA consisting of the nucleotide sequence represented by SEQ ID: No.1;or, the DNA consisting of the nucleotide sequence represented by SEQ ID: No.27; may be exemplified.

The present promoter DNA may for example be isolated using a PCR with a genome DNA from a soybean such as Glycine max as a template.

Specifically, a genome DNA is extracted from a tissue, such as a leaf, of a soybean such as Glycine max. A method for extraction may be a CTAB method described by H.Uchimiya (Plant gene engineering manual, Methods for producing transgenic plants (KODANSHA SCIENTIFIC), 1990, ISBN4-06-153513-7, C3045, p71–74) or an urea-phenol method described by S. O. Rogers and A. U. Bendich (Plant Mol. Biol., 5:69 (1985)). Using as a template a genome DNA thus obtained and also using as primers the oligonucleotide having the nucleotide sequence of nucleotide numbers1743 to 1782 of SEQ ID: No.1 and the oligonucleotide having the nucleotide sequence complementary to the nucleotide sequence of nucleotide numbers 2270 to 2301 of SEQ ID: No.1 to perform a PCR, a DNA consisting of the nucleotide sequence of nucleotide numbers 1743 to 2301 in the nucleotide sequence represented by SEQ ID: No.1 or a DNA, for example of about 0.6 Kb such as a DNA consisting of the nucleotide sequence of nucleotide numbers 1742 to 2300 in the nucleotide sequence represented by SEQ ID: No.26, a DNA consisting of the nucleotide sequence of nucleotide numbers 1744 to 2302 in the nucleotide sequence represented by SEQ ID: No.28 or a DNA consisting of the nucleotide sequence of nucleotide numbers 1742 to 2300 in the nucleotide sequence represented by SEQ ID: No.29, in which one or more nucleotides are deleted from, substituted in or added to the nucleotide sequence of the DNA represented by SEQ ID: No.1 may be amplified. In this case, it may be performed according to a method for introducing s site-specific mutation into DNA, as described later, such as a gapped duplex method, a kunkel method or the like if required. For example, such PCR may be performed in a reaction mixture of 50 $\mu$l, containing 5 $\mu$l of 10×Ex Taq buffer (TaKaRa), 4 $\mu$L of 2.5 mM dNTP mixture (containing each 2.5 mM dATP, dGTP, dCTP, dTTP, each final concentration at 0.2 mM), 0.25 to 1.25 $\mu$l of each 20 $\mu$M primer (final concentration ranging from 0.1 to 0.5 $\mu$M), 0.1 to 0.5 $\mu$g of a template genome DNA and 1.25 units of Ex Taq polymerase (TaKaRa), which is subjected to a cycle involving 94° C. for 1 minute followed by 55° C. for 2 minutes followed by 72° C. for 5 minutes, the cycle being repeated 30 times in total. Alternatively, an oligonucleotide employed as a primer as described above may be designed on the basis of the nucleotide sequence represented by SEQ ID: No.1 to obtain a DNA consisting of a part of the nucleotide sequence represented by SEQ ID: No.1 or a DNA in which one or more nucleotides are deleted from, substituted in or added to the nucleotide sequence of the DNA described above by PCR. At the 5' terminal of a primer employed in PCR, a recognition sequence of restriction enzyme may be added.

The amplified DNA may be cloned into a vector according to a conventional method such as one described in "Molecular Cloning: A Laboratory Manual 2nd edition." (1989), Cold Spring Harbor Laboratory Press, "Current Protocols in Molecular Biology" (1987), John Wiley & Sons, Inc. ISBNO-471-50338-X and the like. Typically, for example, a plasmid vector contained in a TA cloning kit manufactured by Invitogen or a pBluescriptII manufactured by Stratagene may be utilized for the cloning.

Also in the method described above, by performing PCR using as primers the oligonucleotide having the nucleotide sequence of nucleotide numbers1020 to 1050 of SEQ ID: No.1 and the oligonucleotide having the nucleotide sequence complementary to the nucleotide sequence of nucleotide numbers 2270 to 2301 of SEQ ID: No. 1 instead of using as primers the oligonucleotide having the nucleotide sequence of nucleotide numbers1743 to 1782 of SEQ ID: No.1 and the oligonucleotide having the nucleotide sequence complementary to the nucleotide sequence of nucleotide numbers 2270 to 2301 of SEQ ID: No.1, a DNA having the nucleotide sequence of nucleotide numbers 1020 to 2301 of SEQ ID: No.1 and a DNA, for example of about 1.3 Kpb such as a DNA consisting of the nucleotide sequence of nucleotide numbers 1020 to 2300 in the nucleotide sequence represented by SEQ ID: No.26, a DNA consisting of the nucleotide sequence of nucleotide numbers 1022 to 2302 in the nucleotide sequence represented by SEQ ID: No.28 or a DNA consisting of the nucleotide sequence of nucleotide numbers 1019 to 2300 in the nucleotide sequence represented by SEQ ID: No.29, in which one or more nucleotides are deleted from, substituted in or added to the nucleotide sequence of the DNA represented by SEQ ID: No. 29 may be amplified. In this case, it may be performed according to a method for introducing a site-specific mutation into DNA, as described later, such as a gapped duplex method, a kunkel method or the like if required. The amplified DNA may be cloned into a vector by a method described above.

Further, by performing PCR using as primers the oligonucleotide having the nucleotide sequence of nucleotide numbers2 to 32 of SEQ ID: No.1 and the oligonucleotide having the nucleotide sequence complementary to the nucleotide sequence of nucleotide numbers 2270 to 2301 of SEQ ID: No. 1 instead of using as primers the oligonucleotide having the nucleotide sequence of nucleotide numbers1 to 1743 of SEQ ID: No.1 and the oligonucleotide having the nucleotide sequence complementary to the nucleotide sequence of nucleotide numbers 2270 to 2301 of SEQ ID: No.1, a DNA having the nucleotide sequence of nucleotide numbers 2 to 2301 of SEQ ID: No.1 and a DNA, for example of about 2.3 Kpb such as a DNA consisting of the nucleotide sequence of nucleotide numbers 2 to 2300 in the nucleotide sequence represented by SEQ ID: No.26, a DNA consisting of the nucleotide sequence of nucleotide numbers 2 to 2302 in the nucleotide sequence represented by SEQ ID: No.28 or a DNA consisting of the nucleotide sequence of nucleotide numbers 2 to 2300 in the nucleotide sequence represented by SEQ ID: No.29, in which one or more nucleotides are deleted from, substituted in or added to the nucleotide sequence of the DNA represented by SEQ ID: No.1 may be amplified. In this case, it may be performed according to a method for introducing a site-specific mutation into DNA, as described later, such as a gapped duplex method, a kunkel method or the like if required. The amplified DNA may be cloned into a vector by a method described above.

In a case that a DNA of a long sequence is amplified using PCR as described above, one or more nucleotides are occasionally deleted from, substituted in or added to the nucleotide sequence of the amplified DNA depending upon the characteristic of Ex Taq polymerase. In order to isolate a DNA having a desired nucleotide sequence, PCR using plural sets of primers having a sequence corresponding to a part of a desired sequence may be performed. A technique is described in, for example, K. Shimamoto and T. Sasaki (supervisors): A separate volume of Cell Engineering, Plant Cell Engineering Series No. 7, Experimental Protocols for PCR in Model Plants (new version) (SHUJUNSHA) (ISBN4-87962-173-0 C3345, 1997), page 151 to 158 and the like.

Typically, the following method may be utilized in order to isolate a DNA consisting of the nucleotide sequence represented by SEQ ID: No.1.

(Acquisition of a DNA of About 0.6 kbp)

In the first step, by performing PCR using as a template the isolated genome DNA and also using as primers the oligonucleotide having the nucleotide sequence of nucleotide numbers 2027 to 2063 of SEQ ID: No.1 and the oligonucleotide having the nucleotide sequence complementary to the nucleotide sequence of nucleotide numbers 2270 to 2301 of SEQ ID: No. 1, a PCR product of about 280 bp may be obtained. Next, by performing PCR using as a template the isolated genome DNA and also using as primers the oligonucleotide having the nucleotide sequence of nucleotide numbers 1743 to 1782 of SEQ ID: No.1 and the oligonucleotide having the nucleotide sequence complementary to the nucleotide sequence of nucleotide numbers 2027 to 2063 of SEQ ID: No. 1, a PCR product of about 320 bp may be obtained. After mixing two PCR products (about 280 bp, about 320 bp) described above, the resultant is blunted at 3'-terminal end using Klenow flagment (TaKaRa), a PCR product of about 0.6 kbp having the nucleotide sequence of nucleotide numbers1743 to 2301 of SEQ ID: No.1 may be obtained by performing PCR using as a template the resultant mixture thus obtained and also using as primers the oligonucleotide having the nucleotide sequence of nucleotide numbers 1743 to 1782 of SEQ ID: No.1 and the oligonucleotide having the nucleotide sequence complementary to the nucleotide sequence of nucleotide numbers 2270 to 2301 of SEQ ID: No. 1. The PCR product thus obtained may be cloned to a vector according to the method similar to that described above.

(Acquisition of a DNA of About 1.3 kbp)

First, by performing PCR using as a template the isolated genome DNA and also using as primers the oligonucleotide having the nucleotide sequence of nucleotide numbers 1020 to 1058 of SEQ ID: No.1 and the oligonucleotide having the nucleotide sequence complementary to the nucleotide sequence of nucleotide numbers 1197 to 1239 of SEQ ID: No. 1, a PCR product of about 220 bp may be obtained. Next, by performing PCR using as a template the isolated genome DNA and also using as primers the oligonucleotide having the nucleotide sequence of nucleotide numbers 1320 to 1361 of SEQ ID: No.1 and the oligonucleotide having the nucleotide sequence complementary to the nucleotide sequence of nucleotide numbers 1576 to 1618 of SEQ ID: No. 1, a PCR product of about 300 bp may be obtained. Next, by performing PCR using as a template the isolated genome DNA and also using as primers the oligonucleotide having the nucleotide sequence of nucleotide numbers 1576 to 1618 of SEQ ID: No.1 and the oligonucleotide having the nucleotide sequence complementary to the nucleotide sequence of nucleotide numbers 1747 to 1782 of SEQ ID: No. 1, a PCR product of about 210 bp may be obtained. Next, by performing PCR using as a template the isolated genome DNA and also using as primers the oligonucleotide having the nucleotide sequence of nucleotide numbers 1197 to 1239 of SEQ ID: No.1 and the oligonucleotide having the nucleotide sequence complementary to the nucleotide sequence of nucleotide numbers 1320 to 1361 of SEQ ID: No. 1, a PCR product of about 170 bp may be obtained. After mixing four PCR products (about 220 bp, about 300 bp, about 210 bp, about 170 bp) described above and the PCR product (about 0.6 kbp) obtained in the first step, the resultant is blunted at 3'-terminal end using Klenow flagment (TaKaRa), a PCR product of about 1.3 kbp having the nucleotide sequence of nucleotide numbers 1020 to 2301 of SEQ ID: No.1 may be obtained by performing PCR using as a template the resultant mixture thus obtained and also using as primers the oligonucleotide having the nucleotide sequence of nucleotide numbers 1020 to 1058 of SEQ ID: No.1 and the oligonucleotide having the nucleotide sequence complementary to the nucleotide sequence of nucleotide numbers 2270 to 2301 of SEQ ID: No. 1. The PCR product thus obtained may be cloned into a vector according to the method similar to that described above.
(Acquisition of a DNA of About 2.3 kbp)

By performing PCR using as a template the isolated genome DNA and also using as primers the oligonucleotide having the nucleotide sequence of nucleotide numbers 2 to 40 of SEQ ID: No.1 and the oligonucleotide having the nucleotide sequence complementary to the nucleotide sequence of nucleotide numbers 1081 to 1117 of SEQ ID: No. 1, a PCR product of about 1.1 kbp may be obtained. After mixing the PCR product (about 1.1 kbp) and the PCR product (about 1.3 kbp) described above, having the nucleotide sequence of nucleotide numbers 1020 to 230 1 of SEQ ID: No.1 is blunted at 3'-terminal end using Klienow flagment (TaKaRa), a PCR product of about 2.3 kbp having the nucleotide sequence of nucleotide numbers 2 to 2301 of SEQ ID: No.1 may be obtained by performing PCR using as a template the resultant DNA mixture thus obtained and also using as primers the oligonucleotide having the nucleotide sequence of nucleotide numbers 2 to 40 of SEQ ID: No.1 and the oligonucleotide having the nucleotide sequence complementary to the nucleotide sequence of nucleotide numbers 2270 to 2301 of SEQ ID: No. 1. The PCR product thus obtained may be cloned into a vector according to the method similar to that described above.

Further, the following method may be used in order to isolate a DNA consisting of the nucleotide sequence represented by SEQ ID: No. 28.
(Acquisition of a DNA of About 0.6 kbp)

By performing PCR using as a template the isolated genome DNA and also using as primers the oligonucleotide having the nucleotide sequence of nucleotide numbers 1744 to 1783 of SEQ ID: No. 28 and the oligonucleotide having the nucleotide sequence complementary to the nucleotide sequence of nucleotide numbers 2271 to 2302 of SEQ ID: No. 28, a PCR product of about 0.6 kbp having the nucleotide sequence of nucleotide numbers 1744 to 2302 of SEQ ID: No. 28 may b e obtained.
(Acquisition of a DNA of About 1.3 kb p)

Next, by performing PCR using as a template the isolated genome DNA and also using as primers the oligonucleotide having the nucleotide sequence of nucleotide numbers 1022 to 1067 of SEQ ID: No. 28 and the oligonucleotide having the nucleotide sequence complementary to the nucleotide sequence of nucleotide numbers 2271 to 2302 of SEQ ID: No. 28, a PCR product of about 1.3 kbp having the nucleotide sequence of nucleotide numbers 1022 to 2302 of SEQ ID: No. 28 may be obtained.
(Acquisition of a DNA of About 2.3 kbp)

Next, by performing PCR using as a template the isolated genome DNA and also using as primers the oligonucleotide having the nucleotide sequence of nucleotide numbers 2 to 40 of SEQ ID: No. 28 and the oligonucleotide having the nucleotide sequence complementary to the nucleotide sequence of nucleotide numbers 544 to 583 of SEQ ID: No. 28, a PCR product of about 580 bp may be obtained. Next, by performing PCR using as a template the isolated genome DNA and also using as primers the oligonucleotide having the nucleotide sequence of nucleotide numbers 589 to 631 of SEQ ID: No. 28 and the oligonucleotide having the nucleotide sequence complementary to the nucleotide sequence of nucleotide numbers 1037 to 1073 of SEQ ID: No. 28, a PCR product of about 480 bp may be obtained. Next, by performing PCR using as a template the isolated genome DNA and also using as primers the oligonucleotide having the nucleotide sequence of nucleotide numbers 544 to 583 of SEQ ID: No. 28 and the oligonucleotide having the nucleotide sequence complementary to the nucleotide sequence of nucleotide numbers 589 to 631 of SEQ ID: No. 28, a PCR product of about 90 bp may be obtained. After mixing three PCR products (about 580 bp, about 480 bp, about 90 bp) described above and the PCR product (about 1.3 kbp) as described above, having the nucleotide sequence of nucleotide numbers 1022 to 2302 of SEQ ID: No. 28 is blunted at 3'-terminal end using Klenow flagment (TaKaRa), a PCR product of about 2.3 kbp having the nucleotide sequence of nucleotide numbers 2 to 2302 of SEQ ID: No. 28 may be obtained by performing PCR using as a template the resultant DNA mixture thus obtained and also using as primers the oligonucleotide having the nucleotide sequence of nucleotide numbers 2 to 40 of SEQ ID: No. 28 and the oligonucleotide having the nucleotide sequence complementary to the nucleotide sequence of nucleotide numbers 2271 to 2302 of SEQ ID: No. 28. The PCR product thus obtained may be cloned into a vector according to the method similar to that described above.

Moreover, the following method may be used in order to isolate a DNA consisting of the nucleotide sequence represented by SEQ ID: No. 29.
(Acquisition of a DNA of About 0.6 kbp)

By performing PCR using as a template the isolated genome DNA and also using as primers the oligonucleotide having the nucleotide sequence of nucleotide numbers 1742 to 1781 of SEQ ID: No. 29 and the oligonucleotide having the nucleotide sequence complementary to the nucleotide sequence of nucleotide numbers 2269 to 2300 of SEQ ID: No. 29, a PCR product of about 0.6 kbp having the nucleotide sequence of nucleotide numbers 1742 to 2300 of SEQ ID: No. 29 may be obtained.
(Acquisition of a DNA of About 1.3 kbp)

Next, by performing PCR using as a template the isolated genome DNA and also using as primers the oligonucleotide having the nucleotide sequence of nucleotide numbers 1019 to 1057 of SEQ ID: No. 29 and the oligonucleotide having the nucleotide sequence complementary to the nucleotide sequence of nucleotide numbers 1196 to 1238 of SEQ ID: No. 29, a PCR product of about 220 bp may be obtained. Next, by performing PCR using as a template the isolated genome DNA and also using as primers the oligonucleotide having the nucleotide sequence of nucleotide numbers 1491 to 1531 of SEQ ID: No. 29 and the oligonucleotide having the nucleotide sequence complementary to the nucleotide sequence of nucleotide numbers 2269 to 2300 of SEQ ID: No. 29, a PCR product of about 810 bp may be obtained. Next, by performing PCR using as a template the isolated genome DNA and also using as primers the oligonucleotide having the nucleotide sequence of nucleotide numbers 1196 to 1238 of SEQ ID: No. 29 and the oligonucleotide having the nucleotide sequence complementary to the nucleotide sequence of nucleotide numbers 1487 to 1531 of SEQ ID: No. 29, a PCR product of about 340 bp may be obtained. After mixing three PCR products (about 220 bp, about 810 bp, about 340 bp) described above is blunted at 3'-terminal end using Klenow flagment (TaKaRa), a PCR product of about 1.3 kbp having the nucleotide sequence of nucleotide numbers 1019 to 2300 of SEQ ID: No. 29 may be obtained by performing PCR using as a template the resultant DNA mixture and also using as primers the oligonucleotide having the nucleotide sequence of nucleotide numbers 1019 to 1057 of SEQ ID: No. 29 and the oligonucleotide having the nucleotide sequence complementary to the nucleotide sequence of nucleotide numbers 2269 to 2300 of SEQ ID: No. 29. The PCR product thus obtained may be cloned into a vector according to the method similar to that described above.

(Acquisition of a DNA of About 2.3 kbp)

Next, by performing PCR using as a template the isolated genome DNA and also using as primers the oligonucleotide having the nucleotide sequence of nucleotide numbers 2 to 40 of SEQ ID: No. 29 and the gonucleotide having the nucleotide sequence complementary to the nuceleotide sequence of nucleotide numbers 369 to 409 of SEQ ID: No. 29, a PCR product of about 410 bp may be obtained. Next, by performing PCR using as a template the isolated genome DNA and also using as primers the oligonucleotide having the nucleotide sequence of nucleotide numbers 496 to 530 of SEQ ID: No. 29 and the oligonucleotide having the nucleotide sequence complementary to the nucleotide sequence of nucleotide numbers 588 to 628 of SEQ ID: No. 29, a PCR product of about 130 bp may be obtained. Next, by performing PCR using as a template the isolated genome DNA and also using as primers the oligonucleotide having the nucleotide sequence of nucleotide numbers 657 to 699 of SEQ ID: No. 29 and the oligonucleotide having the nucleotide sequence complementary to the nucleotide sequence of nucleotide numbers 752 to 793 of SEQ ID: No. 29, a PCR product of about 140 bp may be obtained. Next, by performing PCR using as a template the isolated genome DNA and also using as primers the oligonucleotide having the nucleotide sequence of nucleotide numbers 752 to 793 of SEQ ID: No. 29 and the oligonucleotide having the nucleotide sequence complementary to the nucleotide sequence of nucleotide numbers 1034 to 1070 of SEQ ID: No. 29, a PCR product of about 320 bp may be obtained. Next, by performing PCR using as a template the isolated genome DNA and also using as primers the oligonucleotide having the nucleotide sequence of nucleotide numbers 369 to 409 of SEQ ID: No. 29 and the oligonucleotide having the nucleotide sequence complementary to the nucleotide sequence of nucleotide numbers 496 to 530 of SEQ ID: No. 29, a PCR product of about 160 bp may be obtained. Next, by performing PCR using as a template the isolated genome DNA and also using as primers the oligonucleotide having the nucleotide sequence of nucleotide numbers 588 to 628 of SEQ ID: No. 29 and the oligonucleotide having the nucleotide sequence complementary to the nucleotide sequence of nucleotide numbers 657 to 699 of SEQ ID: No. 29, a PCR product of about 110 bp may be obtained. After mixing six PCR products (about 410 bp, about 130 bp, about 140 bp, about 320 bp, about 160 bp, about 110 bp) described above and the PCR product (about 1.3 kbp) described above, having the nucleotide sequence of nucleotide numbers 1019 to 2300 of SEQ ID: No. 29 is imparted with a blunt end at 3'-terminal side using Klenow flagment (TaKaRa), a PCR product of about 2.3 kbp having the nucleotide sequence of nucleotide numbers 2 to 2300 of SEQ ID: No. 29 may be obtained by performing PCR using as a template the resultant mixture thus obtained and also using as primers the oligonucleotide having the nucleotide sequence of nucleotide numbers 2 to 40 of SEQ ID: No. 29 and the oligonucleotide having the nucleotide sequence complementary to the nucleotide sequence of nucleotide numbers 2269 to 2300 of SEQ ID: No. 29. The PCR product thus obtained may be cloned into a vector according to the method similar to that described above.

The present promoter DNA may be obtained also by labeling a DNA consisting of at least a part of the nucleotide sequence represented by SEQ ID: No.1, preferably, of about 250 nucleotides or more in length, using the resultant DNA as a probe for hybridization to a DNA derived from a plant, and then detecting and isolating a DNA to which the probe is bound specifically.

Using the method described above, a DNA having a further shorter length than that of the present promoter DNA may be obtained. Such DNA may be utilized as a compact DNA as long as it retains an ability of acting as a promoter, and thus encompassed in one of useful applications of the present promoter DNA.

A DNA to which a probe described above is hybridized may for example be one from a genome DNA library derived from a plant such as soybean. Such DNA library may be obtained as a genome DNA library prepared in accordance with a conventional library preparation method such as one described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X and the like, using a vector such as λFixII, λEMBL3, λEMBL4, λDASHII manufactured by STRATAGENE together with Gigapack packaging Extracts manufactured by STRATAGENE for in vitro packaging. Alternatively, a commercial genome library may also be employed.

A method for hybridizing a probe to a DNA described above may for example be a colony hybridization and a plaque hybridization, and may be selected depending upon the type of the vector employed in the preparation of the library. When the library is constructed using a plasmid vector, a colony hybridization may be performed. Typically, a DNA from the library is introduced into a host microorganism cell to obtain a transformant, which is diluted and inoculated onto an agar medium, which is incubated at 37° C. until a colony is produced. When the library is prepared using a phage vector, a plaque hybridization may be performed. Typically, a host microorganism cell is mixed with a phage in the library in a condition suitable for infection, and then further mixed with a soft agar medium, and the mixture is plated on an agar medium. Thereafter, an incubation is continued at 37° C. until a plaque is produced. More specifically, approximately $9.0 \times 10^5$ pfu of the phage library is spread over an NZY agar medium at a cell density of 0.1 to 1.0 pfu per 1 $mm^2$ of the agar medium in accordance with the method described in "Molecular Cloning: A Laboratory Manual 2nd edition" (1989), Cold Spring Harbor Laboratory Press, page 2.60 to 2.65, and the medium is incubated for 6 to 10 hours at 37° C.

Subsequently, in any of the hybridizations described above, a membrane was placed on the surface of an agar medium which has been incubated as described above to transfer a transformant or a phage onto the membrane. This membrane is treated with an alkali, neutralized, and subjected to an immobilization of a DNA on the membrane. More specifically, in the case of a plaque hybridization, a nitrocellulose membrane or a nylon membrane, such as Hybond-N+ (Amersham), is mounted on an agar medium described above in accordance with a conventional method as described in "Cloning and Sequence: Plant Biotechnology Experiment Manual (Ed. By WATANABE and SUGIURA, NOSONBUNKASHA, 1989), and then allowed to stand for about 1 minute to allow a phage particle to be adsorbed onto the membrane. Subsequently, the membrane is immersed for about 3 minutes in an alkaline solution (1.5 M sodium chloride, 0.5 N NaOH) to allow the phage particle to be solubilized to elute the phage DNA onto the membrane, immersed for about 5 minutes in a neutralization solution (1.5 M sodium chloride, 0.5 M Tris-HCl buffer, pH7.5). Thereafter, the membrane is washed with a washing solution (0.3M sodium chloride, 30 mM sodium citrate, 0.2 M Tris-HCl buffer pH7.5) for about 5 minutes, and then baked, for example, at approximately 80° C. for about 90 minutes, whereby immobilizing the phage DNA onto the membrane.

Using the membrane, a hybridization is performed using the DNA described above as a probe. The hybridization may be performed in accordance with the method described in D. M. Glover (Ed), "DNA cloning, A practical Approach", IRL Press (1985), ISBN 0-947946-18-7, "Cloning and Sequence: Plant Biotechnology Experiment Manual (Ed. By WATANABE and SUGIURA, NOSONBUNKASHA, 1989), or J.Sambrook, E. F. Frisch, T. Maniatis, "Molecular Cloning: A Laboratory Manual 2nd edition (1989)", Cold Spring Harbor Laboratory Press.

In order to label a DNA to be used as a probe with a radioactive isotope, a Random Labeling Kit manufactured by Boehringer Mannheim or TaKaRa may for example be employed, and the labeling may also be performed by PCR in the presence of $(\alpha-^{32}P)dCTP$ instead of dCTP in a conventional PCR reaction mixture and using as a template a DNA which is used as a probe. When a DNA which is used as probe is labeled with a fluorescent dye, an ECL Direct Nucleic Acid Labeling and Detection System manufactured by Amersham may for example be employed.

While various reagents and temperatures are employed for a hybridization, a prehybridization solution containing 450 to 900 mM sodium chloride and 45 to 90 mM sodium citrate, 0.1 to 1.0% sodium dodecylsulfate (SDS), 0 to 200 µg/ml of a modified non-specific DNA, optionally with albumin, ficoll, polyvinylpyrrolidone and the like each at a concentration of 0 to 0.2%, preferably, a prehybridization solution containing 900 mM sodium chloride, 90 mM sodium citrate, 1.0% SDS and 100 µg/ml modified calf-thymus DNA is provided in a volume of 50 to 200 µL per 1 cm² of a membrane prepared as described above, and the membrane is kept as being immersed in this solution for 1 to 4 hours at 42 to 65° C., preferably for 2 hours at 65° C. Subsequently, a hybridization solution containing 450 to 900 mM sodium chloride and 45 to 90 mM sodium citrate, 0.1 to 1.0% SDS, 0 to 200 µg/ml of a modified non-specific DNA, optionally with albumin, ficoll, polyvinylpyrrolidone and the like each at a concentration of 0 to 0.2%, preferably, a hybridization solution containing 900 mM sodium chloride, 90 mM sodium citrate, 1.0% SDS and 100 µg/ml modified calf-thymus DNA and a probe prepared as described above (in an amount corresponding to $1.0 \times 10^4$ to $2.0 \times 10^6$ cpm per 1 cm² of the membrane) is provided in a volume of 50 to 200 µL per 1 cm² of the membrane, and the membrane is immersed in this solution for 12 to 20 hours at 42 to 65° C., preferably for 16 hours at 65° C., whereby accomplishing the hybridization. After this hybridization, the membrane is taken out and washed for 15 minutes twice with a solution containing 15 to 300 mM sodium chloride, 1.5 to 30 mM sodium citrate and 0.1 to 1.0% SDS at 42 to 65° C., preferably with a solution containing 15 mM sodium chloride, 1.5 mM sodium citrate and 1.0% SDS at 65° C. Thereafter, the membrane is rinsed gently with 2×SSC solution (300 mM sodium chloride, 30 mM sodium citrate) and then dried. This membrane is subjected, for example, to an autoradiography to detect the radioactivity of the probe on the membrane, whereby detecting where the DNA which is hybridized with the probe is located on the membrane. A clone corresponding to the location of the DNA detected on the membrane is identified on the agar medium employed initially, and is picked up to isolate the clone having the relevant DNA. Typically, for example, the membrane is exposed to an imaging plate (Fuji Film) for about 4 hours, and then the imaging plate is analyzed using BAS2000 (Fuji Film) to detect a signal. The region (about 5 mm in diameter) where the signal is detected in the agar medium used for preparing the membrane is excised and immersed in about 0.5 mL of SM buffer (50 mM Tris-HCl pH7.5, 0.1 M sodium chloride, 7 mM magnesium sulfate, 0.01% gelatin) for 2 to 16 hours, preferably for 3 hours, to elute a phage particle. The obtained phage particle is spread on an agar medium in accordance with the method described in J. Sambrook, E. F. Frisch, T. Maniatis, "Molecular Cloning: A Laboratory Manual 2nd edition" (1989), Cold Spring Harbor Laboratory Press, page 2.60 to 2.65, and incubated for 6 to 10 hours at 37° C. This agar medium is used to immobilize a phage DNA onto a membrane by the method similar to that described above and this membrane and the probe described above are used to perform a hybridization. The region where the signal is detected in the agar medium used for preparing this membrane is allowed to release a phage particle which is then spread on an agar medium, and the membrane is prepared in a manner similar to that described above, and then a hybridization is performed. By repeating this procedure involving the identification and purification of a phage clone, a phage clone containing a DNA having a nucleotide sequence which can be hybridized with the probe can be obtained.

As a result of the screening by hybridization described above, a DNA derived from the obtained clone may be subcloned into a plasmid vector with which a DNA preparation or analysis may readily be conducted, such as commercially available pUC118, pUC119, pBLUESCRIPT KS+, pBLUESCRIPT KS and the like.

A clone isolated as described above is used to prepare a plasmid DNA, which may be sequenced by a dideoxyterminator method described in F. Sanger, S. Nicklen, A. R. Coulson, "Proceeding of Natural Academy of Science U.S.A. (1977)", 74:5463–5467. A sample for sequencing may be prepared using commercial reagents such as those included in ABI PRISM Dye Terminator Cycle Sequencing Ready Reaction Kit available from Perkin Elmer or equivalent. Alternatively, a sample for sequencing may be prepared in accordance with the primer extension method described in J. Sambrook, E. F. Frisch, T. Maniatis, "Molecular Cloning: A Laboratory Manual 2nd edition" (1989), Cold Spring Harbor Laboratory Press, page 13.15.

A reporter gene, for example, a β-glucuronidase gene is ligated downstream of the DNA obtained as described above and cloned into a vector as desired. Introduction of the DNA into a plant cell is performed by a particle gun method or an Agrobacterium infection method described later, and then the expression of the reporter gene is investigated to determine a promoter activity, i.e., a promoter function of the relevant DNA in the plant cell. For example, a cell extract is prepared from a plant cell such as a tobacco cultured cell line BY-2 into which a DNA described above has been introduced and its β-glucuronidase activity is determined enzymatically, or such cell is immersed in a staining solution containing 5-bromo-4-chloro-3-indolyl-β-D-glucuronic acid to observe the pigmentation of a blue color, whereby determining whether this DN A possesses the promoter function or not, thus obtaining the present promoter DNA. Also by introducing the DNA ligated to a reporter gene as described above into a plant cell such as a tobacco wil d type cell, from which a plant is regenerated and each tissue of this plant or its descendant is examined for its β-glucuronidase activity, or a tissue or its section of this plant or its descendant is immersed in a staining solution containing 5-bromo-4-chloro-3-indolyl-β-D-glucuronic acid to observe the pigmentation of a blue color, whereby examining the promoter function of this DNA, thus obtaining the present promoter DNA. Such reporter gene may not only be a β-glucuronidase gene but also be a luciferase gene, a chloramphenicol acetyltransferase gene, a green fluorescent protein gene and the like.

The present promote r DNA may be obtained also by introducing a mutation into a nucleotide sequence of the DNA consisting of the nucleotide sequence represented by SEQ ID: No.1. Typically, a mutation may randomly be introduced into the DNA consisting of the nucleotide sequence represented by SEQ ID: No.1 by the method described in A. Greener, M. Callahan, Strategies, 1994, Vol.7, page 32 to 34. Also by means of a gapped duplex method described in W. Kramer, et al., Nucleic Acids Research, 1984, Vol.12, page 9441 or W. Kramer, H. J. Frits, Methods in Enzymology, 1987, Vol.154, page 350 and the like, or a Kunkel method described in T. A. Kunkel, Proc. of Natl. Acad. Sci. USA, 1985, Vol.82, page 488, T. A. Kunkel, et al., Methods in Enzymology, 1987, Vol.154, page 367 and the like, a mutation may site-specifically be introduced into the DNA consisting of the nucleotide sequence represented by SEQ ID: No.1. By performing PCR using the DNA consisting of the nucleotide sequence represented by SEQ ID: No.1 as a template and an oligonucleotide having the nucleotide sequence in which one or more nucleotides are deleted from, substituted in or added to a part of the nucleotide sequence represented by SEQ ID: No.1 as a primer, a DNA consisting of a nucleotide sequence in which one or more nucleotides are deleted from, substituted in or added to the nucleotide sequence represented by SEQ ID: No.1 may be amplified. Alternatively, a chimeric DNA in which the nucleotide sequence in one or more regions of the nucleotide sequence represented by SEQ ID: No.1 is substituted by a part of the nucleotide sequence of another promoter may also be prepared. Furthermore, a DNA having a nucleotide sequence in which a part of the nucleotide sequence represented by SEQ ID: No.1 is deleted may be prepared by the method described in S.Henikoff, et al., Gene, 1984, Vol.28, page 351 or C.Yanisch-Perron, et al., Gene, 1985, Vol.33, page 103. By examining the promoter function of the obtained DNA, the present promoter DNA may be obtained.

The present promoter may contain either the present promoter DNA (a) or (b) obtained as described above, or may contain both of the DNAs (a) and (b), may also contain them repetitively.

The present promoter may also contain a nucleotide sequence which enhances a transcription efficiency of a gene in a plant. Such nucleotide sequence may for example be a sequence which enhances constitutionally a transcription in a plant, a sequence which enhances species-specifically tissue-specifically or stage-specifically a transcription in a plant, or a sequence which enhances a transcription in response to an infection with a pathogenic microorganism or by a stress such as light, heat, drought, salt or injury. A nucleotide sequence which enhances the transcription efficiency of a gene in a plant may for example be the transcription activation sequence in which the region from the 318th to 138th nucleotides upstream of the transcription initiation site of a mannopine synthase gene is ligated downstream of the region from the 333rd to 116th nucleotides upstream of the transcription initiation site of an octopine synthase gene of Agrobacterium, the transcription activation sequence in which the region from the 333rd to 116th nucleotides upstream of the transcription initiation point of an octopine synthase gene is ligated downstream of the region from the 318th to 213th nucleotides upstream of the transcription initiation site of a mannopinee synthase gene (The Plant Journal, 7(4):661–676(1995)), the nucleotide sequence comprising the 343rd to 91st nucleotides upstream of the transcription initiation site of a cauliflower mosaic virus 35S promoter (Nature, 313:810–812 (1985)), the nucleotide sequence comprising the 1099th to 205th sites upstream of the transcription initiation point of a small subunit gene (rbc-3A) of tomato ribulose-1,5-diphosphate carboxylase-oxidase (Plant Cell, 1:217–227 (1990)), the nucleotide sequence comprising the 902nd to 287th nucleotides upstream of the transcription initiation site of tobacco PR1a gene (Plant Cell, 2:357–366 (1990)), and the nucleotide sequence comprising the 1300th to 195th nucleotides upstream of the transcription initiation site of a potato protease inhibitor gene (PI-II) (Plant Cell, 2:61–70 (1990)).

The present promoter may also comprise a nucleotide sequence having a transcription activation sequence which is comprised in the nucleotide sequence represented by SEQ ID: No.1. Once such nucleotide sequence is identified, the present promoter comprising such nucleotide sequence repetitively can also be prepared, or, it may be ligated to other DNA having a promoter function in a plant cell to produce a novel plant promoter. In order to identify such nucleotide sequence, a reporter gene may for example be expressed in a plant cell under the control of any of the present promoter DNAs, and the expression levels are compared, whereby analyzing a nucleotide sequence contributing to transcription activation. More typically, a plural number of a DNA consisting of a nucleotide sequence in which one or more nucleotides are deleted from or substituted in the nucleotide sequence represented by SEQ ID: No.1 may for example be prepared and each is ligated at the position downstream thereof with a reporter gene, such as a β-glucuronidase gene, and then introduced into a plant cell such as a tobacco cultured cell BY-2 using a particle gun method or an Agrobacterium infection method. Subsequently, from the obtained cell, a cell extract is prepared and its β-glucuronidase activity is enzymatically determined, or such cell is immersed in a staining solution containing 5-bromo-4-chloro-3-indolyl-β-D-glucuronic acid to observe the pigmentation of a blue color to examine the expression level of the reporter gene in each cell and the obtained results are compared with the nucleotide sequence of the DNA ligated to the reporter gene as described above, whereby identifying a nucleotide sequence contributing to transcription activation. Also by introducing a DNA ligated to a reporter gene as described above into a plant cell such as a tobacco wild type cell, from which a plant is regenerated and each tissue of this plant or its descendant is examined for its β-glucuronidase activity, or a tissue or its section of this plant or its descendant is immersed in a staining solution containing 5-bromo-4-chloro-3-indolyl-β-D-glucuronic acid to observe the pigmentation of a blue color whereby comparing the expression level of the reporter gene controlled by each DNA described above, thus identifying a nucleotide sequence contributing to transcription activation.

In order to express a desired gene in a plant cell using the present promoter, a gene in which the present promoter, the desired gene and a terminator are ligated in a functional form (hereinafter referred to as the present chimeric gene) may be utilized.

The desired gene referred herein means a gene to be expressed in a plant, for example, a gene encoding a protein such as an enzyme, a storage protein, a receptor, a transcription regulating factor, a signal transduction factor and the like. Such gene is bound downstream of the present promoter in the sense- or antisense-direction as desired. A terminator means a DNA which exerts a transcription termination in a cell such as a plant cell subjected to the DNA introduction, such as a terminator of a nopaline synthase gene derived from a Ti-plasmid of a bacterium of Agrobacterium (NOS), a terminator derived from a plant virus such as garlic viruses GV1 and GV2 and the like. The present chimeric gene may comprise the nucleotide sequence of the present promoter or a part thereof repetitively. The term "in a functional form" means that when the present chimeric gene is introduced to transform a cell such as a plant cell an desired gene contained in this chimeric gene is ligated with the present promoter and a terminator so that it can be expressed under the control of these promoter and terminator.

In the context of a vector having the present promoter, the vector means a DNA which can replicate in a cell such as a plasmid, a phage, a phagemid and the like which can be proliferated in a cell such as E.coli, yeasts, plant cells and animal cells, which may be selected depending upon the host cell employed or the intended use. Those exemplified specifically includes pUC plasmids (pUC118, pUC119 (TaKaRa)), pSC101 plasmids, Ti-plasmids (pBI101, pBI121 (CLONTECH)), Bluescript phagemids (pBluescript SK(+/−) (STRATAGENE)), M13 phages (mp10, mp11 (Amersham)), λ phages (λgt10, gt11 (Amersham)), cosmids (SuperCosI (STRATAGENE)) and the like, into which the present promoter is introduced whereby constructing a vector having the present promoter.

A vector having the present promoter described above is more convenient for constructing a vector which expresses a desired gene in a plant cell when a gene insertion site and a terminator exist downstream of this promoter. A gene insertion site referred herein means, for example, a nucleotide sequence which can be recognized and cleaved specifically by a restriction enzyme employed usually in a gene engineering technology, preferably a restriction enzyme recognition sequence which is the only sequence on a vector having the present promoter and a terminator. Such gene insertion site, the present promoter and the terminator are positioned preferably so that when a desired gene is inserted into the gene insertion site the present promoter, the desired gene and the terminator are connected on the vector in a functional form. Such vector may for example be constructed by inserting the present promoter DNA into a multicloning site (gene insertion site) of a plasmid containing a gene insertion site and a terminator, typically, pBI101.3 (CLONTECH) and the like. Alternatively, such vector may be constructed by inserting the present promoter and a terminator into a multicloning site (gene insertion site) of a vector having a gene insertion site, typically, pBIN19 (Nucl. Acid Res. 12:8711–8721 (1984)) and the like.

A vector having the present chimeric gene may be utilized to introduce this chimeric gene into a host cell. Such vector may for example be prepared by cloning the present chimeric gene into a vector exemplified above, or cloning a desired gene into a gene insertion site of a vector having the present promoter, the gene insertion site and a terminator as those described above. Typically, a vector produced by inserting the present promoter DNA into a multicloning site (gene insertion site) of, for example, pBI101.3 (CLONTECH) is cleaved with a restriction enzyme to remove a reporter gene (β-glucuronidase) in this vector, instead of which a desired gene is inserted, whereby preparing a vector having the present chimeric gene.

The present vector as described above may contain not only the present promoter, a desired gene to be expressed and a terminator, but also a marker gene for selecting a host cell into which the vector is introduced (for example, kanamycin-resistant gene, hygromycin-resistant gene, neomycin-resistant gene, a gene which can impart a plant with a herbicide-resistant activity, and the like). In addition, such vector may contain the nucleotide sequence of the present promoter repetitively.

The present vector may for example be introduced into a microorganism of E.coli or Agrobacterium by a calcium chloride method or an electroporation method described in J. Sambrook, E. F. Frisch, T. Maniatis, "Molecular Cloning", 2nd edition (1989), Cold Spring Harbor Laboratory, and the resultant microorganism cell into which the present vector has been introduced (transformant) is useful for preparation of a DNA of the present chimeric gene and for introduction of such chimeric gene into a plant cell.

A DNA encoding the present promoter and a DNA of the present chimeric gene may be introduced into a plant cell also by a particle gun method (a direct introduction of a DNA into a tissue cell or a cultured cell using a particle gun). Furthermore, the present vector may be introduced into a plant cell by a known method such as an Agrobacterium infection method (a method for infecting a plant tissue with an Agrobacterium microorganism), an electric introduction (an electroporation or an electric introduction into a protoplast) and a particle gun method.

Examples of a plant cell into which the present promoter, the present chimeric gene or the present vector is introduced and in which the gene may be expressed under the control of the present promoter are a cell derived from a monocotyledonous plant such as rice, maize, barley and wheat as well as a cell derived from a dicotyledonous plant such as a leguminous plant including soybean, pea, bean or alfalfa, a solanaceous plant such as tobacco, tomato and potato, a brassicaceous plant such as cabbage, rape or leaf mustard, a cucurbitaceous plant such as melon, pumpkin and cucumber, a umbelliferous plant such as carrot and celery, and a composite plant such as lettuce.

By introducing the present promoter, the present chimeric gene or the present vector into a plant cell and by obtaining a transformant as described above, a plant cell in which the present promoter is inserted upstream of a desired gene on a genome DNA and which expresses this gene under the control of the present promoter, a plant cell in which the present chimeric gene is inserted on a genome DNA and which expresses a desired gene contained in this chimeric gene under the control of the present promoter, and a plant cell which has a vector having the present chimeric gene in the cell and expresses a gene contained in this chimeric gene under the control of the present promoter may be obtained.

The transformed plant may be regenerated according to a method used in a conventional plant tissue culture technology such as those described in S. B. Gelvin, R. A. Schilperoot and D. P. S. Verma: Plant Molecular Biology Manual, Kluwer, Academic Publishers press (1988), K. Shimamoto and K. Okada (supervisors): Experimental protocols in model plants (rice, Arabidopsis thaliana) (SHUJUNSHA) (ISBN4-87962-157-9 C3345, 1996), page 78 to 143 or H. UCHIMIYA, Plant gene engineering manual, Methods for producing transgenic plants (KODANSHA SCIENTIFIC), 1990, ISBN4-06-153513-7, C3045, page 28 to 33, whereby obtaining a transformed plant or a part thereof which is derived from the plant cell described above. Furthermore, by cultivating and propagating the obtained plant, a descendant of this plant may be obtained.

In addition, by extracting a genome DNA according to a conventional method from a plant cell or a plant transformed as described above, cleaving the genome DNA with a restriction enzyme and performing a southern hybridization using as a probe a DNA employed for introducing into a host cell or a part thereof, the introduced gene may be identified. Furthermore, by extracting an RNA according to a standard method from a plant cell or a plant described above and then performing a northern hybridization using as a probe an oligonucleotide or a DNA derived from a gene which is expected to be expressed under the control of the present promoter, the condition of the expression of the desired gene may be investigated.

Under the control of the present promoter, a particular gene may be positioned in the sense- or antisense direction and can be expressed in a plant. A gene to be expressed may for example be a storage protein gene such as soybean glycinin gene, β-conglycinin gene, Brazil nut 2S albumin gene or maize or rice 10 kDa protein gene or 15 kDa protein gene, a biotin biosynthesis-related enzyme gene such as bioA gene, bioB gene, bioC gene, bioD gene, bioF gene or bioH gene derived from a microorganism such as *E.coli,* a lipid metabolism-related gene such as stearoyl-ACP-desaturase gene, acyl-ACP-thioesterase gene, 3-phosphate acyltransferase gene or acyltransferase gene, an amylopectine decomposing enzyme gene such as those of rice isomerases as well as a raffinose family oligosaccharide synthase gene.

EXAMPLES

The present invention is further described in the following examples which are not intended to restrict the invention.

Example 1
(Genome DNA Preparation)

A genome DNA was prepared by a CTAB method described in H. Uchimiya, Plant gene engineering manual, Methods for producing transgenic plants (KODANSHA SCIENTIFIC), 1990, ISBN4-06-153513-7, C3045, p71–74 from a piece of a leaf of soybean (Glycine max cv. Williams). Approximately 0.5 g of the plant leaf was ground in an Eppfendorf tube thoroughly using a homogenizer and then mixed with 0.5 ml of a 2×CTAB solution [2% cetyltrimethyl ammonium bromide, 100 mM Tris-HCl, pH 8.0, 20 mM EDTA, 1.4 M NaCl, 1% polyvinylpyrrolidone (PVP)] which had previously been kept at 65° C., and the mixture was kept at 65° C. for 5 minutes. This was combined with 0.5 mL of a chloroform/isoamylalcohol (24:1) mixture and mixed gently for 5 minutes. The mixture was centrifuged for 10 minutes at 12,000 rpm (10,000×g) to isolate the supernatant, which was combined with a 1/10 volume of a 10% CTAB solution (10% cetyltrimethyl ammonium bromide, 0.7 M NaCl) which was kept at 65° C., and the mixture was kept at 65° C. for 3 minutes. To this mixture, an equal volume of a chloroform/isoamylalcohol (24:1) mixture was added and mixed thoroughly, and the supernatant was isolated. To this supernatant, 2 volumes of a CTAB sedimentation solution (1% cetyltrimethyl ammonium bromide, 50 mM Tris-HCl, pH8.0, 10 mM EDTA) was added, and the mixture was kept at 65° C. for 1 minute, and then centrifuged for 10 minutes at 12,000 rpm (10,000×g) to precipitate a DNA. The obtained precipitation was dissolved in 50 μl of a TE at a high salt concentration (10 mM Tris-HCl, pH8.0, 1 mM EDTA, 1M NaCl) and combined with 100 μL of ethanol and mixed thoroughly. The mixture was centrifuged for 15 minutes at 12,000 rpm (10,000×g) to obtain a precipitation, which was dissolved in 50 μL of TE (10 mM Tris-HCl, pH8.0, 1 mM EDTA). To this mixture, an RNase was added up to 10 μg/mL, and the mixture was kept at 37° C. for 30 minutes, and then combined with an equal volume of a phenol/chloroform/isoamylalcohol (25:24:1) mixture and mixed thoroughly, and then the supernatant was isolated. This was combined with 1/10 volume of 3 M sodium acetate solution (pH 5.2) and 2.5 volumes of ethanol and mixed thoroughly, and centrifuged for 5 minutes at 12,000 rpm (10,000×g) to obtain about 5 μg of a genome DNA.

Example 2
(Acquisition of the Present Promoter by Inverse PCR)

450 ng of the isolated genome DNA in Example 1 was digested with a restriction enzyme EcoT22I completely and then a ligation (15° C., 10 hours) was conducted using T4 DNA ligase (TaKaRa). Then the DNA was recovered using an ethanol precipitation and dissolved in 20 μl of sterilized water.

5 μl aliquot of this solution was subjected to PCR (94° C. for 1 minute, followed by 55° C. for 2 minutes, followed by 72° C. for 3 minutes in 1 cycle, the cycle being repeated 30 times in total) using the oligonucleotide consisting of the nucleotide sequence represented by SEQ ID: No.3 (SRS-5R) and the oligonucleotide consisting of the nucleotide sequence represented by SEQ ID: No.4 (SRS-6) as primers together with Ex Taq polymerase (TaKaRa). A 1/10 volume aliquot of the PCR reaction solution thus obtained was subjected again to PCR (94° C. for 1 minute, followed by 55° C. for 2 minutes, followed by 72° C. for 3 minutes in 1 cycle, the cycle being repeated 30 times in total) using the oligonucleotide consisting of the nucleotide sequence represented by SEQ ID: No.5 (SRS-6R) and the oligonucleotide consisting of the nucleotide sequence represented by SEQ ID: No.2 (SRS-5) as primers together with Ex Taq polymerase (TaKaRa). The DNA contained in the PCR reaction solution thus obtained was subjected to a 0.8% agarose gel electrophoresis, which revealed an amplification of approximately 3 kbp DNA. This DNA of approximately 3 kbp was recovered from the gel, digested with EcoT22I, and then blunted using T4 DNA polymerase. Subsequently, this DNA was mixed with a HincII-digested product of plasmid pUC119 (TaKaRa) and ligated using T4 DNA ligase (TaKaRa). After this ligation, the obtained DNA was introduced into an *E.coli* JM109 (competent cell produced by TaKaRa) and three clones having a plasmid containing an about 3 kbp DNA were isolated, which was then analyzed for its nucleotide sequences. The analysis of the nucleotide sequence involved a PCR performed by a dye terminator method employing a fluorescent dideoxynucleotide (Applied Biosystems) followed by a sequencing by a fluorescent DNA sequencer (Applied Biosystems, Model 373A). The primers for determining the nucleotide sequence were M13 primers (TaKaRa) and an oligonucleotide consisting of the nucleotide sequence represented by any of SEQ ID: Nos.6 to 18. The nucleotide sequence in the approximately 0.6 kbp region in the approximately 3 kbp DNA contained in each of the three clones described above was same as the nucleotide sequence after the initiation codon in the coding region of a raffinose synthase gene derived from a soybean (European Patent Application No.0849359). The approximately 2.4 kbp nucleotide sequence upstream of the coding region which was derived from one of three clones is represented by SEQ ID: No.1 or 27. This upstream nucleotide sequence involved difference in 13 positions (in a case of SEQ ID: No.1) and in 16 positions (in a case of SEQ ID: No.27) among the three clones described above. Then, using the isolated genome DNA in Example 1 as a template together with the primers which were the oligonucleotide consisting of the nucleotide sequence represented by SEQ ID: No.9 (SRS-16) and the oligonucleotide consisting of the nucleotide sequence represented by SEQ ID: No.10 (SRS-17), the oligonucleotide consisting of the nucleotide sequence represented by SEQ ID: No.11 (SRS-18) and the oligonucleotide consisting of the nucleotide sequence represented by SEQ ID: No.12 (SRS- 19), the oligonucleotide consisting of the nucleotide sequence represented by SEQ ID: No.8 (SRS-15) and the oligonucleotide consisting of the nucleotide sequence represented by SEQ ID: No.17 (SRS-31), the oligonucleotide consisting of the nucleotide sequence represented by SEQ ID: No.12 (SRS-19) and the oligonucleotide consisting of the nucleotide sequence represented by SEQ ID: No.30 (SRS-26) or the oligonucleotide consisting of the nucleotide sequence represented by SEQ ID: No.13 (SRS-20) with the oligonucleotide consisting of the nucleotide sequence represented by SEQ ID: No.25 (SRS-21), and also using Ex Taq polymerase (TaKaRa), PCR (94° C. for 1 minute, followed by 55° C. for 2 minutes, followed by 72° C. for 3 minutes in 1 cycle, the cycle being repeated 30 times in total) was conducted. The obtained DNA was blunted using T4 DNA polymerase, and this DNA was mixed with a HincII-digested product of plasmid pUC119 (TaKaRa) and ligated using T4 DNA ligase (TaKaRa). After this ligation, the obtained DNA was introduced into an *E.coli* JM109 (competent cell produced by TaKaRa) and subjected to a screening to obtain a plasmid containing the DNA obtained from the PCR described above, whose DNA was then analyzed for its nucleotide sequences. The analysis of the nucleotide sequence involved PCR performed by a dye terminator method employing a fluorescent dideoxynucleotide (Applied Biosystems) followed by sequencing by a fluorescent DNA sequencer (Applied Biosystems, Model 373A) similarly to the procedure described above. The primers for determining the nucleotide sequence were M13 primers (TaKaRa). The nucleotides at the 16 positions in total exhibiting the difference among the three clones described above (the nucleotide sequence of the DNA of each clone was represented by SEQ ID: No.27, 28 or 29) were identified. The identified nucleotide sequence upstream of the coding region is represented by SEQ ID: No.26.

The nucleotides of the 16 positions exhibiting the difference are listed below.

1. "A" which is nucleotide number 389 in SEQ ID: No.26
   It corresponds to "G" which is nucleotide number 389 in SEQ ID: No. 29.
2. "A" which is nucleotide number 515 in SEQ ID: No.26
   It corresponds to "G" which is nucleotide number 515 in SEQ ID: No. 29.
3. a position between "T" which is nucleotide number 563 and "A" which is Bases No. 564 in SEQ ID: No.26
   It corresponds to (inserted) "T" which is nucleotide number 564 in SEQ ID: No. 28
4. "A" which is nucleotide number 609 in SEQ ID: No.26
   It corresponds to a deletion at a position of nucleotide number 609 in SEQ ID: No. 29.
5. a position between of "A" which is nucleotide number 609 and "C" which is Bases No. 610 in SEQ ID: No.26
   It corresponds to (inserted) "A" which is nucleotide number 611 in SEQ ID: No. 28
6. "T" which is nucleotide number 679 in SEQ ID: No.26
   It corresponds to "C" which is nucleotide number 678 in SEQ ID: No. 29.
7. "C" which is nucleotide number 774 in SEQ ID: No.26
   It corresponds to "T" which is nucleotide number 773 in SEQ ID: No. 29.
8. "T" which is nucleotide number 1052 in SEQ ID: No.26
   It corresponds to "A" which is nucleotide number 1054 in SEQ ID: No. 28.
9. a position between of "T" which is nucleotide number 1215 and "A" which is Bases No. 1216 in SEQ ID: No.26
   It corresponds to (inserted) "T" which is nucleotide number 1216 in SEQ ID: No. 27
   It also corresponds to (inserted) "T" which is nucleotide number 1215 in SEQ ID: No. 29
10. "T" which is nucleotide number 1340 in SEQ ID: No.26
    It corresponds to "C" which is nucleotide number 1341 in SEQ ID: No. 27.
11. "T" which is nucleotide number 1511 in SEQ ID: No.26
    It corresponds to "C" which is nucleotide number 1511 in SEQ ID: No. 29.
12. "A" which is nucleotide number 1596 in SEQ ID: No.26
    It corresponds to "G" which is nucleotide number 1597 in SEQ ID: No. 27.
13. "T" which is nucleotide number 2045 in SEQ ID: No.26
    It corresponds to "C" which is nucleotide number 2046 in SEQ ID: No. 27.
14. "C" which is nucleotide number 2332 in SEQ ID: No.26
    It corresponds to "T" which is nucleotide number 2333 in SEQ ID: No. 27.
15. "T" which is nucleotide number 2333 in SEQ ID: No.26
    It corresponds to "C" which is nucleotide number 2333 in SEQ ID: No. 29.
16. "G" which is nucleotide number 2357 in SEQ ID: No.26
    It corresponds to "A" which is nucleotide number 2358 in SEQ ID: No. 27.

Example 3
(Construction of the Present Vector for Expressing Luciferase)

The DNA of the plasmid having the DNA consisting of the nucleotide sequence represented by SEQ ID: No.1 which is one of the three clones obtained in Example 2 was digested with NdeI, BglII or EcoT22I and then each end was blunted using T4 DNA polymerase. These DNAs were digested further with NcoI to isolate 0.6 kbp, 1.4 kbp and 2.4 kbp DNAs (hereinafter designated as the present promoter DNAs 1 to 3).

Thus, the present promoter DNA 1 is the approximately 0.6 kbp DNA consisting of the nucleotide sequence of nucleotide numbers 1743 to 2362 in the nucleotide sequence represented by SEQ ID: No. 27;

the present promoter DNA 2 is the approximately 1.4 kbp DNA consisting of the nucleotide sequence of nucleotide numbers 1020 to 2362 in the nucleotide sequence represented by SEQ ID: No. 27;and, the present promoter DNA 3 is the approximately 2.4 kbp DNA consisting of the nucleotide sequence of nucleotide numbers 2 to 2362 in the nucleotide sequence represented by SEQ ID: No. 27.

The HincII-digested product of plasmid pUC118 (TaKaRa) was ligated with an NcoI linker using T4 DNA ligase (the obtained plasmid is designated as pUC118/NcoI). Subsequently, the DNA obtained by digesting pUC118/NcoI with NcoI and HindIII was ligated with the NcoI—HindIII DNA (comprising luciferase gene and soybean glycinin gene terminator region) isolated from a plasmid pSUM-GY1-LUC (Iida et al (1995), Plant Cell Reports 14:539–544), whereby constructing plasmid pUC118-LUC. Then the DNA of this plasmid pUC1 18-LUC was digested with SmaI and NcoI, and the resultant DNA was ligated with each of the present promoter DNAs 1 to 3 (0.6 kbp, 1.4 kbp, 2.4 kbp) using T4 DNA ligase (TaKaRa), whereby constructing the three present vectors for expressing luciferase each of which had the luciferase gene ligated downstream of each of the present promoter DNAs 1 to 3 (pRS1/LUC, pRS2/LUC, pRS3/LUC) (FIG. 1).

Example 4
(Introduction of the Present Vector in Soybean Seed)

Each of the present vectors for expressing luciferase obtained in Example 3 was introduced into a soybean premature seed by a direct introduction method (Yang N-S, Christou P (Ed), Particle Bombardment Technology for Gene Transfer, W. H. Freeman and Co. Publishers, New York, pp.52–59) using a gene gun by Morikawa et al (C. M. Particle Gun System, Rehbock Co., Tokyo, Japan). 0.5 to 1 μm gold particles (Tokuriki Honten Co., Ltd, Japan) were washed several times with ethanol and adjusted at 60 mg/mL in a sterilized water. The present vector for expressing luciferase prepared in Example 3 was mixed with a pBI221 (Clonetech) as an internal standard in the molar ratio of 3:1, and the final DNA concentration was adjusted at 500 μg/ml in a sterilized water. A 20 μL aliquot (DNA 10 μg) was mixed with 50 μl of the gold particle suspension (3 mg of the gold particles), and 50 μl of 2.5M calcium chloride was added and stirred rapidly, and then 20 μl of 0.1M spermidine and stirred rapidly. After allowing to stand for at least 30 minute at room temperature, the mixture was centrifuged gently (9000 rpm, 5 seconds) to precipitate the gold particles. The supernatant was removed and the gold particles were washed with 70% ethanol and then suspended in 50 μL of ethanol. Each of the 10 μL aliquots of this gold particle suspension was mounted on a top of a projectile and dried. The projectile was set on a gene gun and shot at 335 m/sec under vacuum at 110 mmHg into a soybean premature seed placed on an MS agar medium. As a control, only a pBI221 (Clonetech) was shot into a soybean premature seed similarly.

The soybean premature seed into which both of the present vector for expressing luciferase and a pBI221 (Clonetech) or only a pBI221 (Clonetech) had been introduced was homoginized in an extraction buffer solution (0.1 M potassium phosphate, 1 mM DTT, pH7.5) using a pestle and a mortar, and the resultant dispersion was centrifuged at 12,000 rpm (10,000×g). The supernatant was isolated and used for the determination of a luciferase activity. The luciferase activity was determined using PicaGene luminescence kit (TOYO INK) and a luminometer. The supernatant described above and 100 μl of the luminescence reagent were mixed and the luminescence level was determined for 30 seconds by the luminometer. The β-glucuronidase activity was determined using GUS-light kit (TROPIX) and the luminometer. 20 μL of the supernatant described above and 180 μL of the GUS reaction reagent were mixed and allowed to stand for 60 minutes at room temperature, and combined with 300 μL of a luminescence reagent and then the luminescence level was determined for 5 seconds by the luminometer. The luciferase activity was divided by the β-glucuronidase activity (internal standard) to obtain the relative luciferase activity (Table 1). Any of the soybean seeds into which the three present vectors for expressing luciferase were introduced exhibited a relative luciferase activity higher than that exhibited by the soybean seed into which only a pBI221 (Clonetech) was introduced (control).

TABLE 1

| Transduced plasmid | Luciferase activity* |
| --- | --- |
| pRS1/LUC + pBI221 | 40 |
| pRS2/LUC + pBI221 | 25 |
| pRS3/LUC + pBI221 | 50 |
| pBI221 (control) | 1 |

*The relative luciferase activity with the introduction of a pBI221 only The activity of internal standard or control was regarded as 1.

Example 5
(Construction of the Present Binary Vector for Expressing Luciferase)

A binary plasmid pBI101 (Clonetech) is digested with a restriction enzyme EcoRI, and blunted using T4 DNA polymerase (TaKaRa). This is digested further with a restriction enzyme SmaI and a vector DNA in which a GUS gene and a nopaline synthase gene-derived terminator were deleted is recovered by an agarose gel electrophoresis. On the other hand, a plasmid pSUM-GY1 (Iida et al (1995), Plant Cell Reports 14:539–544) is digested with a restriction enzyme HindIII and blunted using T4 DNA polymerase (TaKaRa), and then ligated with an EcoRI linker (TaKaRa) using a DNA ligase (TaKaRa). The obtained DNA is digested with PstI (TaKaRa) and blunted using T4 DNA polymerase (TaKaRa), and then digested with a restriction enzyme EcoRI (TaKaRa), and an about 0.7 kb DNA comprising a soybean glycinin gene terminator region is recovered by an agarose gel electrophoresis. The pBI101-derived vector DNA (EcoRI/SmaI) described above is ligated with an about 0.7 kb DNA comprising a soybean glycinin gene terminator region using a DNA ligase (TaKaRa) to obtain a plasmid pBI101-GY1ter.

Figure 2:
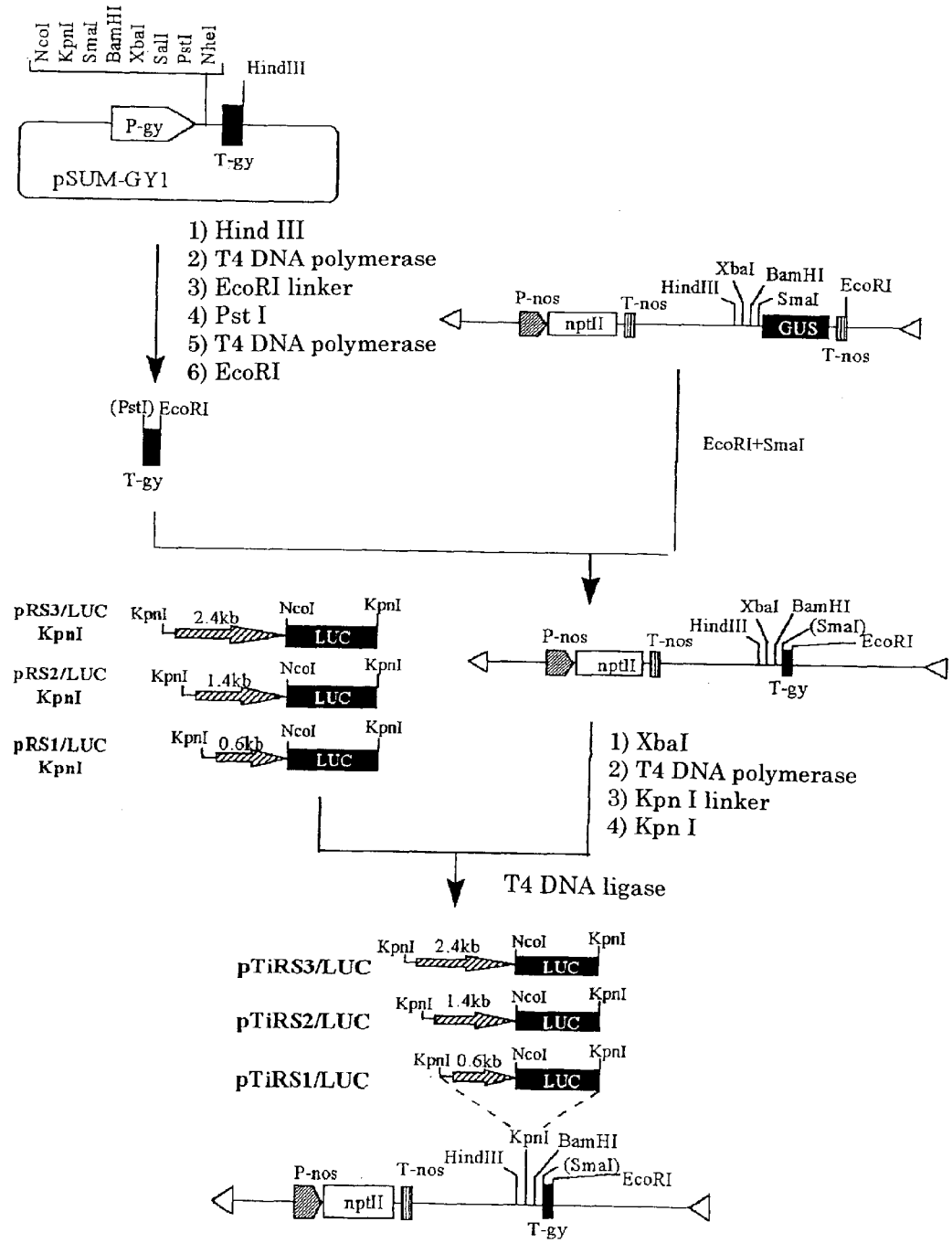
FIG. 2 shows the process for constructing the present binary vectors pTiRS1/LUC, pTiRS2/LUC and pTiRS3/LUC each comprising the present promoter for expressing the luciferase. In this figure, LUC represents a firefly-derived luciferase gene, GUS represents an *E.coli* -derived β-glucuronidase gene, nptII represents an *E.coli* -derived neomycin phosphotransferase gene, P-nos represents a Ti plasmid-derived nopaline synthase gene promoter, P-gy represents a soybean-derived glycinin gene promoter, T-nos represents a Ti plasmid-derived nopaline synthase gene terminator, and T-gy represents a soybean-derived glycinin gene terminator. A restriction enzyme sequence within a bracket indicates a modification of the restriction enzyme recognition sequence in which this restriction enzyme cannot conduct the digestion.

The plasmid pBI101-GY1ter is digested with a restriction enzyme XbaI (TaKaRa) and blunted using T4 DNA polymerase (TaKaRa). This DNA is ligated with a KpnI linker (TaKaRa) using a DNA ligase (TaKaRa), and then digested with a restriction enzyme KpnI. On the other hand, the three present vectors for expressing luciferase prepared in Example 3 are digested with a restriction enzyme KpnI (TaKaRa) and a DNA containing the present promoter DNA and a luciferase gene is recovered by an agarose gel electrophoresis. The obtained DNA is ligated with a Kpn I-digested product of a plasmid pBI101-GY1ter using T4 DNA ligase (TaKaRa) to prepare three binary vectors for expressing luciferase (pTiRS1/LUC, pTiRS2/LUC, pTiRS3/LUC) containing a chimeric gene in which the present promoter DNA, the luciferase gene and the soybean glycinin gene terminator are ligated in this order (FIG. 2).

Example 6
(Construction of the Present Vector for Expressing Raffinose Synthase)

Figure 3:
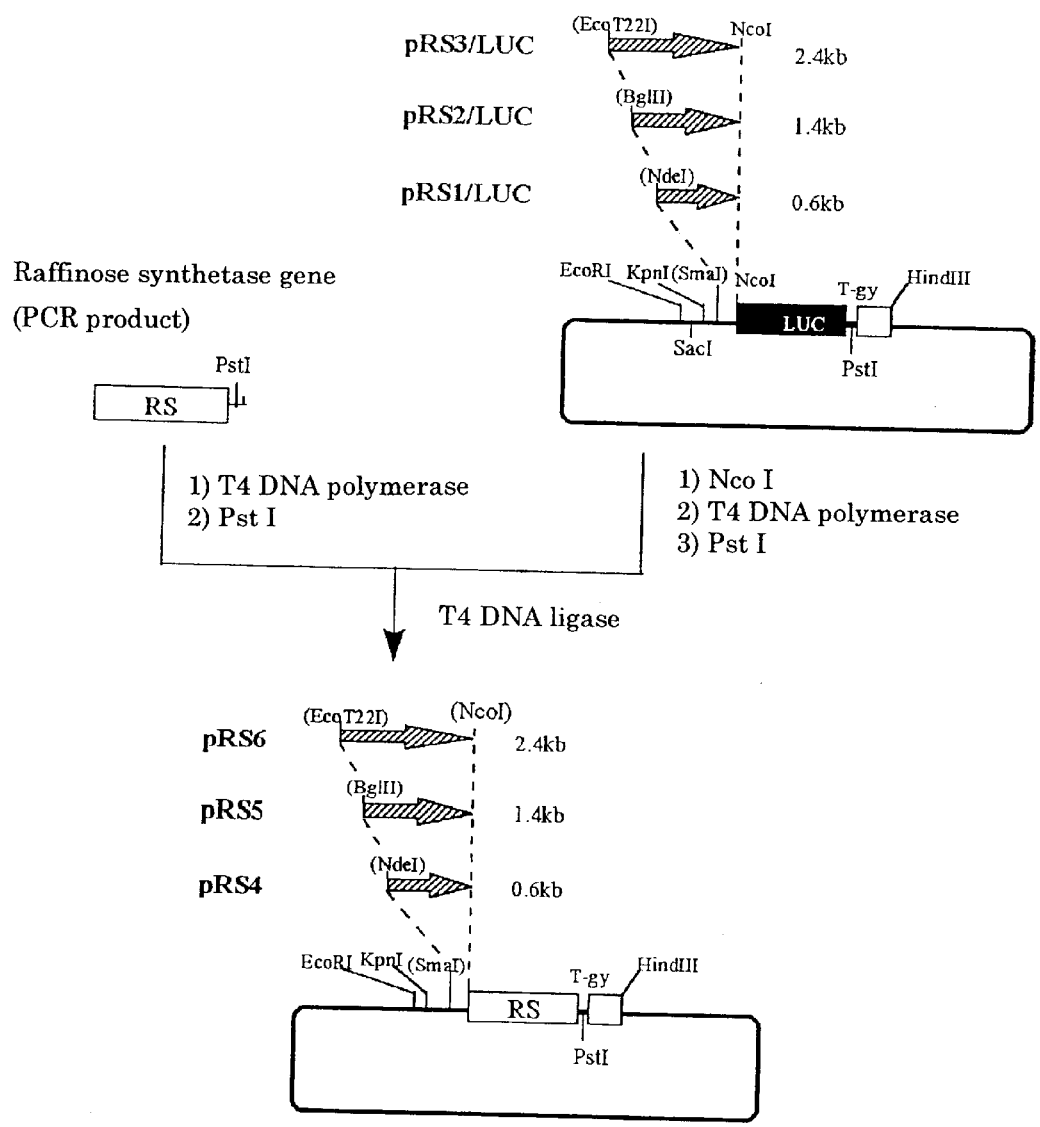
FIG. 3 shows the process for constructing the present vectors pRS4, pRS5 and pRS6 each comprising the present promoter for expressing the raffinose synthase. In this figure, LUC represents a firefly-derived luciferase gene, T-gy represents a soybean-derived glycinin gene terminator, RS represents a soybean-derived raffinose synthase gene. A restriction enzyme site within a bracket indicates a modification of the restriction enzyme recognition sequence in which this restriction enzyme cannot conduct the digestion.

A combination of the oligonucleotide consisting of the nucleotide sequence represented by SEQ ID: No.19 (SRS-N) and the oligonucleotide consisting of the nucleotide sequence represented by SEQ ID: No.20 (4RV) or a combination of the oligonucleotide consisting of the nucleotide sequence represented by SEQ ID: No.21 (seq1) and the oligonucleotide consisting of the nucleotide sequence represented by SEQ ID: No.22 (C2pst) is used as primers with a soybean cDNA library as a template to perform PCR (94° C. for 1 minute, followed by 55° C. for 2 minutes, followed by 72° C. for 3 minutes in 1 cycle, the cycle being repeated 30 times in total). Then 30 ng of each PCR product is mixed and used as templates to perform PCR again with the combination of the oligonucleotide consisting of the nucleotide sequence represented by SEQ ID: No.19 (SRS-N) and the oligonucleotide consisting of the nucleotide sequence represented by SEQ ID: No.22 (C2pst) as primers, whereby obtaining a DNA consisting of the nucleotide sequence of nucleotide numbers61 to 2451 which encodes raffinose synthase in the nucleotide sequence represented by SEQ ID: No.23. The obtained DNA is blunted using Mung Bean Nuclease (TaKaRa) and then digested with a restriction enzyme PstI (TaKaRa). On the other hand, each of the three present vectors for expressing luciferase obtained in Example 3 is digested with a restriction enzyme NcoI and blunted using Mung Bean Nuclease (TaKaRa) and then digested with a restriction enzyme PstI (TaKaRa). This digestion solution is subjected to an agarose electrophoresis, and the present vector DNA in which a luciferase gene is deleted is recovered. The obtained DNA which is derived from the present vector is ligated with the DNA encoding the raffinose synthase described above using T4 DNA ligase (TaKaRa) to obtain the present vectors for expressing raffinose synthase (pRS4, pRS5 and pRS6) (FIG. 3).

Figure 4:
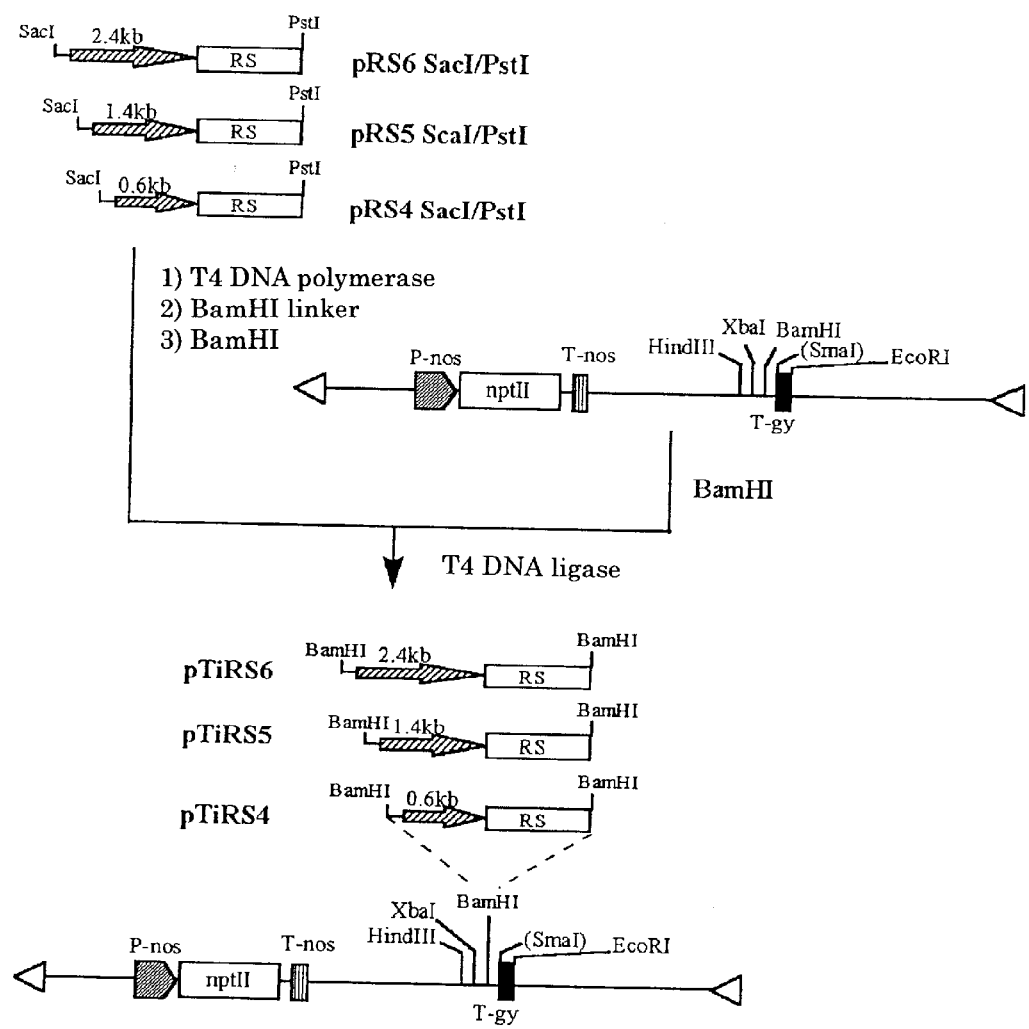
FIG.4 shows the process for constructing the present binary vectors pTiRS4, pTiRS5 and pTiRS6 each comprising the present promoter for expressing the raffinose synthase. In this figure, RS represents a soybean-derived raffinose synthase gene, nptll represents an E.coli -derived neomycin phosphotransferase gene, P-nos represents a Ti plasmid-derived nopaline synthase gene promoter, T-nos represents a Ti plasmid-derived nopaline synthase gene terminator, and T-gy represents a soybean-derived glycinin gene terminator. A restriction enzyme site within a bracket indicates a modification of the restriction enzyme recognition sequence in which this restriction enzyme cannot conduct the digestion.

Each of the present vectors pRS4, pRS5 and pRS6 is digested with restriction enzymes SacI and PstI (TaKaRa) and then a cohesive end is blunted using T4 DNA polymerase (TaKaRa). This DNA is ligated with a BamHI linker (TaKaRa) using T4 DNA ligase (TaKaRa) and digested with a restriction enzyme BamHI (TaKaRa). On the other hand, the plasmid pBI101-GY1ter obtained in Example 5 is digested with a restriction enzyme BamHI (TaKaRa) and ligated with the DNA derived from plasmid pRS4, pRS5 or pRS6 using T4 DNA ligase (TaKaRa) to obtain three binary vectors (pTiRS4, pTiRS5, pTiRS6) in each of which a raffinose synthase gene has been ligated under the control of the present promoter (FIG. 4).

Example 7
(Production of Transformed Tobacco by Indirect Introduction)

Each of the DNAs of the present binary vectors obtained in Examples 5 and 6 is introduced by means of a heat treatment (37° C. for 5 minutes) into Agrobacterium (Agrobacterium tumefaciens LBA4404) (streptomycin-resistant, rifampicin-resistant) (Hoekma et al., Nature, 303:179–180 (1983)) which has been made competent by treatment with 20 mM $CaCl_2$. The Agrobacterium is incubated in an L agar medium containing 300 $\mu$g/ml streptomycin, 100 $\mu$g/ml of rifampicin and 25 $\mu$g/ml of kanamycin to select a transformant imparted with a kanamycin resistance derived from the NPTII gene in the plasmid (Trien-Cuot et al., Gene 23:331–341(1983)).

The transformant of Agrobacterium is incubated overnight in an L medium containing 300 $\mu$g/ml streptomycin, 100 $\mu$g/ml rifampicin and 25 $\mu$g/ml kanamycin and a resultant cell suspension is subjected to the method described in S. B. Gelvin, R. A. Schilperoort and D. P. S. Verma: Plant Molecular Biology Manual (1988) (Published by Kluwer Academic Publishers), H. UCHIMIYA, Plant gene engineering manual, Methods for producing transgenic plants (KODANSHA SCIENTIFIC), 1990, ISBN4-06-153513-7, C3045, page 28 to 33, whereby infecting a piece of tobacco leaf disk with the transformant of Agrobacterium described above.

The piece of the tobacco (SR-1) leaf disk infected with the transformant of Agrobacterium is cultivated for 4 days on an MS-NB agar medium and then transferred to an MS-NB agar medium containing 500 $\mu$g/ml cefotaxim and then cultivated. The leaf is transferred to an MS-NB agar medium containing 500 $\mu$g/ml cefotaxim and 100 $\mu$g/ml kanamycin on the 11th day after inoculation and then further cultivated. After about 4 weeks, a green juvenile plant whose stem and leaf have been regenerated is cut from the piece of the disk, subcultured on an MS-NB medium containing 500 $\mu$g/ml cefotaxim and 50 $\mu$g/ml kanamycin, and a juvenile plant which has emerged is isolated. The isolated tobacco juvenile plant is cultivated in a soil in a green house, whereby obtaining a transformed plant.

Example 8
(Validation of Insertion of Introduced Gene in Transformed Plant)
(1) Preparation of Genome DNA from Transformed Plant From a piece of a leaf of the transformed plant obtained in Example 7, a genome DNA is prepared by a CTAB method described in H. UCHIMIYA, Plant gene engineering manual, Methods for producing transgenic plants (KODANSHA SCIENTIFIC), 1990, ISBN4-06-153513-7, C3045, page 71 to 74. Approximately 0.5 g of the plant leaf is ground in an Eppfendorf tube thoroughly using a homogenizer and then mixed with 0.5 ml of a 2×CTAB solution [2% cetyltrimethyl ammonium bromide, 100 mM Tris-HCl, pH 8.0, 20 mM EDTA, 1.4 M NaCl, 1% polyvinylpyrrolidone (PVP)] which has previously been kept at 65° C., and the mixture is kept at 65° C. for 5 minutes. This is combined with 0.5 mL of a chloroform/isoamylalcohol (24:1) mixture and mixed gently for 5 minutes. The mixture is centrifuged for 10 minutes at 12,000 rpm (10,000×g) to isolate the supernatant, which is combined with a 1/10 volume of a 10% CTAB solution (10% cetyltrimethyl ammonium bromide, 0.7 M NaCl) which is kept at 65° C., and the mixture was kept at 65° C. for 3 minutes. An equal volume of a chloroform/isoamylalcohol (24:1) mixture is added and mixed thoroughly, and the supernatant is isolated. A 2 volumes of a CTAB sedimentation solution (1% cetyltrimethyl ammonium bromide, 50 mM Tris-HCl, pH8.0, 10 mM EDTA) is added, and the mixture is kept at 65° C. for 1 minute, and then centrifuged for 10 minutes at 12,000 rpm (10,000×g) to precipitate a DNA. The precipitation is dissolved in 50 $\mu$l of a TE at a high salt concentration (10 mM Tris-HCl, pH8.0, 1 mM EDTA, 1M NaCl) and combined with 100 $\mu$L of ethanol and mixed thoroughly. The mixture is centrifuged for 15 minutes at 12,000 rpm (10,000×g) to obtain a precipitation, which is dissolved in 50 $\mu$L of TE (10 mM Tris-HCl, pH8.0, 1 mM EDTA). To this mixture, an RNase is added at 10 $\mu$g/mL, and the mixture is kept at 37° C. for 30 minutes, and then combined with an equal volume of a phenol/chloroform/isoamylalcohol (25:24:1) mixture and mixed thoroughly, and then the supernatant is isolated. This was combined with a 1/10 volume of 3 M sodium acetate solution (pH 5.2) and a 2.5 volumes of ethanol and mixed thoroughly, and centrifuged for 5 minutes at 12,000 rpm (10,000×G) to obtain about 5 $\mu$g of a genome DNA.

(2) Validation of Insertion of Introduced Gene by PCR 50 ng of the isolated genome DNA of a tobacco into which each of the present binary vectors prepared in Example 6 (pTiRS4, pTiRS5, pTiRS6) has been introduced is used as a template with the primers which are the oligonucleotide consisting of the nucleotide sequence represented by SEQ ID: No. 16 (SRS-27) and the oligonucleotide consisting of the nucleotide sequence represented by SEQ ID: No.5 (SRS-6R) to perform PCR (94° C. for 1 minute, followed by 55° C. for 2 minutes, followed by 72° C. for 3 minutes in 1 cycle, the cycle being repeated 30 times in total). The obtained PCR product is subjected to an agarose gel electrophoresis, whereby detecting the amplification of an about 800 bp DNA fragment and thus ensuring that a raffinose synthase gene is integrated into a chromosome. In the case of a tobacco into which each of the present binary vectors (pTiRS1/LUC, pTiRS2/LUC, pTiRS3/LUC) obtained in Example 5 has been introduced, a PCR is performed using as primers the oligonucleotide consisting of the nucleotide sequence represented by SEQ ID: No.16 (SRS-27) and the oligonucleotide consisting of the nucleotide sequence represented by SEQ ID: No.24 (1ucl), whereby detecting the amplification of an about 700 bp DNA fragment and thus ensuring that a luciferase gene is integrated into the chromosome.

The composition of each medium employed in the relevant Example is shown below.
1. MS agar medium 34.7 g of MURASHIGE AND SKOOG (Flow Laboratories) was dissolved in 1L of distilled water and adjusted at pH5.8 with 1M KOH, and, after addition of 8 g of agar, sterilized by autoclaving.

25

2. MS-NB agar medium

To an MS agar medium, 0.1 mg/mL of 1-naphthaleneacetic acid (NAA) and 1.0 mg/mL of 6-benzylaminopurine (BA) were added.

3. L medium 10 g of Bactotryptone (Difco), 5 g of Bactoyeast extract (Difco) and 10 g of NaCl were dissolved in 1 L of distilled water and adjusted at pH7.0 with 5 M NaOH and then sterilized by autoclaving. An agar medium was prepared using 15 g of Bactoagar (Difco) aditionally, and then sterilized by autoclaving.

4, NZY medium 10 g of N2 amine (Type A) (WAKO PURE CHEMICAL), 5 g of Bactoyeast extract (Difco) and 5 g of NaCl were dissolved in 1 L of distilled water and adjusted at pH7.0 with 5 M NaOH and then sterilized by ed autoclaving. An agar medium was prepared using 15 g of Bactoagar (Difco) additionally, and then sterilized by autoclaving.

According to the present invention, a novel plant promoter and the like which can be used in a plant breeding technology by a gene introduction can Free Text for Sequence Listing SEQ ID: No.2

Oligonucleotide Primer Designed for PCR

What is claimed is:

1. A promoter comprising an isolated DNA selected from the group consisting of:
   (a) an isolated DNA consisting of the nucleotide sequence of nucleotide numbers 1743 to 2301 in the nucleotide sequence represented by SEQ ID: No. 1; and
   (b) an isolated DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC.

2. A promoter comprising an isolated DNA selected from the group consisting of:
   (a) an isolated DNA consisting of the nucleotide sequence of nucleotide numbers 1020 to 2301 in the nucleotide sequence represented by SEQ ID: No. 1;
   (b) an isolated DNA consisting of the nucleotide sequence of nucleotide numbers 2 to 2301 in the nucleotide sequence represented by SEQ ID: No. 1;
   (c) an isolated DNA consisting of the nucleotide sequence represented by SEQ ID: No. 1; and
   (d) an isolated DNA which can be hybridized in a stringent condition with the DNA of (a), (b) or (c), which can be hybridized in a stringent condition with a DNA consisting of the nucleotide sequence of nucleotide numbers 1743 to 2301 in the nucleotide sequence represented by SEQ ID: No. 1, and which has promoter function in a plant cell, wherein said stringent condition is hybridization at 65° C in 6×SSC, maintained after washing for thirty minutes at 65° C. in 0.1×SSC.

3. A chimeric nucleic acid sequence constructed by ligating
   (1) a promoter comprising a DNA selected from the group consisting of:
      (a) a DNA consisting of the nucleotide sequence of nucleotide numbers 1743 to 2301 in the nucleotide sequence represented by SEQ ID: No. 1; and
      (b) a DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC,
   (2) a desirable nucleic acid sequence and (3) a terminator in a functional form.

4. A vector comprising the chimeric nucleic acid sequence of claim 3.

5. A transformant produced by introducing the chimeric nucleic acid sequence of claim 3 into a host cell.

6. A vector comprising a promoter comprising a DNA selected from the group consisting of:
   (a) a DNA consisting of the nucleotide sequence of nucleotide numbers 1743 to 2301 in the nucleotide sequence represented by SEQ ID: No. 1; and
   (b) a DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC.

7. The vector according to claim 6 comprising a gene insertion site and a terminator downstream of the promoter.

8. A transformant produced by introducing the vector of claim 6 into a host cell.

9. A transformant produced by introducing a promoter comprising a DNA selected from the group consisting of:
   (a) a DNA consisting of the nucleotide sequence of nucleotide numbers 1743 to 2301 in the nucleotide sequence represented by SEQ ID: No. 1; and
   (b) a DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC
into a host cell.

10. The transformant according to claim 9 wherein the host cell is a microorganism cell.

11. The transformant according to claim 9 wherein the host cell is a plant cell.

12. A method for producing a chimeric nucleic acid sequence comprising a step of ligating
   (1) a promoter comprising a DNA selected from the group consisting of:
      (a) a DNA consisting of the nucleotide sequence of nucleotide numbers 1743 to 2301 in the nucleotide sequence represented by SEQ ID: No. 1; and
      (b) a DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC,
   (2) a desired nucleic acid sequence and
   (3) a terminator
in a functional form.

13. A method for producing a vector which comprises a step of ligating
   (1) a promoter comprising a DNA selected from the group consisting of:
      (a) a DNA consisting of the nucleotide sequence of nucleotide numbers 1743 to 2301 in the nucleotide sequence represented by SEQ ID: No. 1; and
      (b) a DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC and
   (2) a desired nucleic acid sequence
in a functional form.

14. A method for producing a transformed plant comprising a step of
   introducing into a plant cell a promoter comprising a DNA selected from the group consisting of:
      (a) a DNA consisting of the nucleotide sequence of nucleotide numbers 1743 to 2301 in the nucleotide sequence represented by SEQ ID: No. 1; and
      (b) a DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC and
   a step of expressing a nucleic acid sequence under the control of said promoter.

15. A promoter comprising an isolated DNA selected from the group consisting of:
   (a) an isolated DNA consisting of the nucleotide sequence of nucleotide numbers 1743 to 2301 in the nucleotide sequence represented by SEQ ID: No. 1;
   (b) an isolated DNA which can be hybridized with the DNA of (a) in a stringent condition and having a promoter function in a plant cell, wherein said stringent condition is hybridization at 65° C. in 6×SSC, maintained after washing for thirty minutes at 65° C. in 0.1×SSC;
   (c) an isolated DNA consisting of the nucleotide sequence of nucleotide numbers 1020 to 2301 in the nucleotide sequence represented by SEQ ID: No. 1;
   (d) an isolated DNA consisting of the nucleotide sequence of nucleotide numbers 2 to 2301 in the nucleotide sequence represented by SEQ ID: No. 1;
   (e) an isolated DNA consisting of the nucleotide sequence represented by SEQ ID; No. 1; and
   (f) an isolated DNA which can be hybridized in a stringent condition with the DNA of (c), (d) or (e), which can be hybridized in a stringent condition with a DNA consisting of the nucleotide sequence of nucleotide numbers 1743 to 2301 in the nucleotide sequence represented by SEQ ID: No. 1, and which has promoter function in a plant cell, wherein said stringent condition is hybridization at 65° C. in 6×SSC, maintained after washing for thirty minutes at 65° C. in 0.1×SSC.

* * * * *